(12) United States Patent
Simanzhenkov et al.

(10) Patent No.: US 12,077,491 B2
(45) Date of Patent: Sep. 3, 2024

(54) STEAM GENERATION IN OXIDATIVE DEHYDROGENATION

(71) Applicant: NOVA CHEMICALS (INTERNATIONAL) S.A., Fribourg (CH)

(72) Inventors: Vasily Simanzhenkov, Calgary (CA); Robert Ladd, Airdrie (CA); Michael Koselek, Red Deer (CA); Kamal Serhal, Calgary (CA); Shahin Goodarznia, Calgary (CA); Bolaji Olayiwola, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 260 days.

(21) Appl. No.: 17/640,582

(22) PCT Filed: Sep. 16, 2020

(86) PCT No.: PCT/IB2020/058631
§ 371 (c)(1),
(2) Date: Mar. 4, 2022

(87) PCT Pub. No.: WO2021/059087
PCT Pub. Date: Apr. 1, 2021

(65) Prior Publication Data
US 2022/0315509 A1    Oct. 6, 2022

Related U.S. Application Data

(60) Provisional application No. 62/904,823, filed on Sep. 24, 2019.

(51) Int. Cl.
*C07C 5/48*    (2006.01)
*B01J 8/06*    (2006.01)

(52) U.S. Cl.
CPC ................. *C07C 5/48* (2013.01); *B01J 8/067* (2013.01); *B01J 2208/00212* (2013.01)

(58) Field of Classification Search
None
See application file for complete search history.

(56) References Cited

U.S. PATENT DOCUMENTS 4,899,003 A    2/1990   Manyik et al.
9,409,156 B2   8/2016   Valente et al.
(Continued)

FOREIGN PATENT DOCUMENTS

WO    WO 2013/092179    6/2013

OTHER PUBLICATIONS

International Preliminary Report on Patentability in International Appln. No. PCT/IB2020/058631, mailed on Mar. 15, 2022, 7 pages.
(Continued)

*Primary Examiner* — Tam M Nguyen
(74) *Attorney, Agent, or Firm* — Fish & Richardson P.C.

(57) ABSTRACT

A system and method for oxidative dehydrogenation including a first reactor having a first ODH catalyst to dehydrogenate an alkane to a corresponding alkene at a first temperature and facilitate generation of steam, a second reactor having a second ODH catalyst to dehydrogenate alkane in a first-reactor effluent to the corresponding alkene at a second temperature that may be greater than the first temperature and facilitate generation of steam, and a third reactor having a third ODH catalyst to dehydrogenate alkane in a second-reactor effluent to the corresponding alkene at a third temperature that may be greater than the first temperature or the second temperature and facilitate generation of steam.

19 Claims, 9 Drawing Sheets

(56) References Cited

U.S. PATENT DOCUMENTS

| | | | |
|---|---|---|---|
| 2014/0371504 A1 | 12/2014 | Stine et al. | |
| 2015/0152024 A1* | 6/2015 | Iitsuka | B01J 29/061 |
| | | | 585/643 |
| 2018/0305278 A1 | 10/2018 | Serhal et al. | |
| 2018/0305289 A1* | 10/2018 | Sookraj | C07D 305/14 |
| 2018/0312614 A1* | 11/2018 | Berbee | C08F 10/02 |
| 2018/0346610 A1* | 12/2018 | Brown | C08F 210/16 |
| 2019/0106532 A1* | 4/2019 | Sookraj | C08G 63/78 |
| 2019/0135956 A1* | 5/2019 | Den Doelder | C09D 123/06 |
| 2019/0169149 A1* | 6/2019 | Teles | B01J 37/0045 |
| 2019/0177443 A1* | 6/2019 | Berbee | C08F 2/38 |
| 2019/0201865 A1* | 7/2019 | Littmann | B01J 19/2415 |
| 2019/0210989 A1* | 7/2019 | Teles | C07D 301/32 |

OTHER PUBLICATIONS

International Search Report and Written Opinion in International Appln. No. PCT/IB2020/058631, mailed on Dec. 10, 2020, 10 pages.

\* cited by examiner

US 12,077,491 B2

STEAM GENERATION IN OXIDATIVE DEHYDROGENATION

CROSS-REFERENCE TO RELATED APPLICATION

This application is a National Stage Application under 35 U.S.C. § 371 and claims the benefit of International Application No. PCT/IB2020/058631, filed Sep. 16, 2020, which claims priority to U.S. Ser. No. 62/904,823, filed Sep. 24, 2019. The disclosure of the prior applications is considered part of and is incorporated by reference in the disclosure of this application.

TECHNICAL FIELD

This disclosure relates to oxidative dehydrogenation and, more particularly, to steam generation via the catalytic oxidative dehydrogenation reaction.

BACKGROUND ART

Catalytic oxidative dehydrogenation of alkanes into corresponding alkenes is an alternative to steam cracking. In contrast to steam cracking, oxidative dehydrogenation (ODH) may operate at lower temperature and generally does not produce coke. For ethylene production, ODH can provide a greater selectivity for ethylene than does steam cracking. The ODH may be performed in a reactor vessel having a catalyst for the conversion of an alkane to a corresponding alkene. The concept of ODH has been known since at least the late 1960's. Since that time, considerable effort has been expended on improving the ODH process and associated catalyst efficiency and selectivity.

SUMMARY OF INVENTION

The following aspects are related to an ODH reactor system. The ODH reactor system includes a first reactor having a first ODH catalyst to dehydrogenate a lower alkane to a corresponding alkene at a first temperature and facilitate generation of steam. The first reactor has a first-reactor jacket for heat transfer. The ODH reactor system includes a second reactor having a second ODH catalyst to dehydrogenate unreacted lower alkane in a first-reactor effluent from the first reactor to the corresponding alkene at a second temperature greater than the first temperature and facilitate generation of steam. The second reactor has a second-reactor jacket for heat transfer. The ODH reactor system includes a third reactor having a third ODH catalyst to dehydrogenate unreacted lower alkane in a second-reactor effluent from the second reactor to the corresponding alkene at a third temperature greater than the second temperature and facilitate generation of steam. The third reactor has a third-reactor jacket for heat transfer.

Another aspect relates to a system for oxidative dehydrogenation. The system includes a first reactor having a first ODH catalyst to dehydrogenate an alkane at a first temperature. The first reactor has a first-reactor jacket to heat a first heat-transfer fluid flowing through the first-reactor jacket to facilitate generation of steam. The system includes a second reactor having a second ODH catalyst to dehydrogenate unreacted alkane from the first reactor at a second temperature greater than the first temperature. The second reactor has a second-reactor jacket to heat a second heat-transfer fluid flowing through the second-reactor jacket to facilitate generation of steam. The system includes a third reactor having a third ODH catalyst to dehydrogenate unreacted alkane from the second reactor at a third temperature greater than the first temperature. The third reactor has a third-reactor jacket to heat a third heat-transfer fluid flowing through the third-reactor jacket to facilitate generation of steam. The third ODH catalyst and the second ODH catalyst are different than the first ODH catalyst.

Yet another aspect relates to a method of oxidative dehydrogenation. The method includes contacting a feed having a lower alkane with a first ODH catalyst in a first reactor at a first temperature to dehydrogenate the lower alkane into a corresponding alkene and to heat a first heat-transfer fluid flowing through a first-reactor jacket to facilitate generation of steam. The method includes contacting a first-reactor effluent from the first reactor with a second ODH catalyst in a second reactor at a second temperature greater than the first temperature to dehydrogenate unreacted lower alkane from the first-reactor effluent into the corresponding alkene and to heat a second heat-transfer fluid flowing through a second-reactor jacket to facilitate generation of steam. The method includes contacting a second-reactor effluent from the second reactor with a third ODH catalyst in a third reactor at a third temperature greater than the first temperature to dehydrogenate unreacted lower alkane from the second effluent into the corresponding alkene and to heat a third heat-transfer fluid flowing through a third-reactor jacket to facilitate generation of steam.

The details of one or more implementations are set forth in the accompanying drawings and the description below. Other features and advantages will be apparent from the description and drawings, and from the claims.

BRIEF DESCRIPTION OF DRAWINGS

Like reference numbers and designations in the various drawings indicate like elements.

DESCRIPTION OF EMBODIMENTS

The catalytic oxidative dehydrogenation (ODH) reaction is exothermic. Therefore, steam may be generated as a coproduct in utilizing heat from the ODH reaction. The steam production may be characterized as integrated with or within the ODH reactor system. In addition, the usage of the produced steam may be integrated at the site having the ODH reactor system. The produced steam may be utilized in the overall ODH system or in other unit operations or units at the facility having the ODH system. The produced steam may also be exported for use by other facilities or sites.

Different qualities or pressures of steam may be generated as a coproduct of the ODH reaction. The term "quality" of the steam may refer to the pressure or type of steam. Typical qualities of steam produced are low pressure steam (e.g., 150 pounds per square inch gauge [psig] or less), medium pressure steam (e.g., in the range of 150 psig to 600 psig), high pressure steam (e.g., 600 psig or greater), or very high pressure steam (e.g., 1500 psig or greater), and so forth. There may be different applications for the steam. The use of the steam by the consumers or customers receiving the steam may depend on the quality or pressure of the steam. In some implementations, higher steam pressures of the produced steam may give more versatility in the integration of the steam within the facility or plant. For instance, high pressure steam is used to power turbines attached to compressors, while low pressure steam is typically used for heating purposes, and the like.

In some implementations, two or more ODH reactors in series may operate at progressively higher temperature to generate different qualities of steam. The respective operating temperature of the ODH reactors may be increasingly greater along the series of ODH reactors. The second ODH reactor may have a higher operating temperature than the first ODH reactor. The third ODH reactor may have a higher operating temperature than the second ODH reactor, and so on.

The different reaction temperatures among the respective ODH reactors may be due to utilization of different types or grades of catalysts in the respective ODH reactors. The catalyst in the second ODH reactor may give an ODH reaction at a greater temperature than the catalyst in the first ODH reactor. The catalyst in the third ODH reactor may give an ODH reaction at a greater temperature than the catalyst in the second ODH reactor, and so on.

Three ODH reactors are depicted in the ODH reactor systems of FIGS. 1-8. However, the present ODH reactor systems may have only two ODH reactors in series or may have more than three ODH reactors (e.g., four ODH reactors, five ODH reactors, etc.) in series or parallel for the generation of steam. The final ODH reactor in the series may discharge an effluent having a product alkene of the ODH reactor system.

Figure 1:
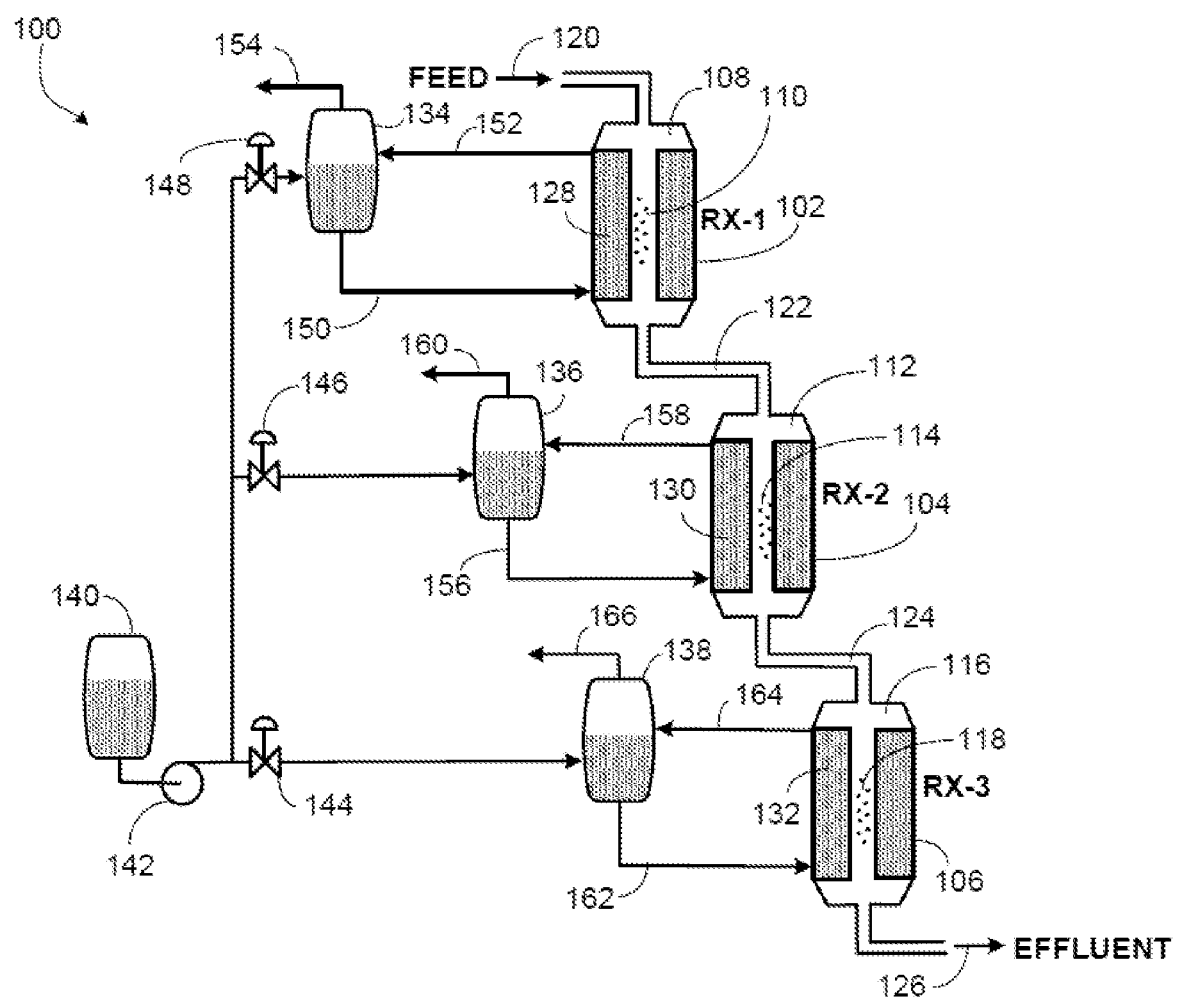
FIGS. 1-8 are diagrams of respective ODH reactor systems each having three ODH reactors operationally disposed in series.

FIG. 1 is an ODH reactor system 100 including a first ODH reactor 102, a second ODH reactor 104, and a third ODH reactor 106 operationally disposed in series. In the illustrated embodiment, the ODH reactors 102, 104, 106 are tubular reactors having a process side and a cooling jacket. The process side is one or more tubes or conduits for the reaction of the alkane to alkene. The process side has catalyst (e.g., a fixed bed of catalyst) for the conversion of the alkane to the corresponding alkene. The system 100 flows water as a heat transfer fluid through the jacket side to control the reaction temperature on the process side. The heat or energy acquired by the heat transfer fluid through the reactor jacket may be utilized to generate steam as a coproduct. For the system 100 in operation, the liquid water is depicted with gray shading in FIG. 1. Such gray shading for liquid water is also utilized in FIGS. 2-8.

The first ODH reactor 102 has a process side 108 having a first catalyst 110. The second ODH reactor 104 has a process side 112 having a second catalyst 114. The third ODH reactor 106 has a process side 116 having a third catalyst 118. As indicated, each process side 108, 112, 116 may be one or more conduits or tubes in some examples. The first catalyst 110, second catalyst 114, and third catalyst 118 may each be a fixed bed of catalyst. The first catalyst 110, second catalyst 114, and third catalyst 118 may be the same catalyst type or different respective catalyst types.

In operation, the process side 108 of the first ODH reactor 102 may receive a feed 120 having an alkane. The feed 120 as a hydrocarbon feed may also include oxygen for the ODH reaction. However, the oxygen may be added to the first ODH reactor separate from the feed 120. The alkane in the feed 120 may be a lower alkane defined as an alkane (saturated hydrocarbon) having a number of carbons in the range of 2 to 6. The first ODH reactor 102 may receive the feed 120 via a conduit coupled (e.g., by a flanged connection) to an inlet of the first ODH reactor 102 vessel at the process side 108. The first ODH reactor 102 may convert the alkane in the feed 120 to a corresponding alkene in a catalytic reaction via the catalyst 110 on the process side 108 of the first reactor 102. Some of the alkane in the feed 120 is not converted into the corresponding alkene but remains unreacted. The first ODH reactor 102 discharges an effluent 122 having the corresponding alkene and unreacted alkane. In one implementation, the alkane is ethane and the corresponding alkene is ethylene. In that implementation, the effluent 122 may also include acetic acid. In addition, the effluent 122 may include carbon dioxide, water, and so forth.

The process side 112 of the second ODH reactor 104 may receive (e.g., via a conduit) the effluent 122 from the first ODH reactor 102. The second ODH reactor 104 may convert the unreacted alkane to the corresponding alkene in a catalytic reaction via the catalyst 114 on the process side 112 of the second reactor 104. Some of the unreacted alkane is not converted into the corresponding alkene but remains unreacted. The second ODH reactor 104 discharges an effluent 124 having the corresponding alkene and unreacted alkane.

The process side 116 of the third ODH reactor 106 may receive (e.g., via a conduit) the effluent 124 from the second ODH reactor 104. The third ODH reactor 106 may convert the unreacted alkane to the corresponding alkene in a catalytic reaction with the catalyst 118 on the process side 116 of the third reactor 106. The third ODH reactor 106 discharges an effluent 126 having the corresponding alkene and any unreacted alkane. The corresponding alkene (e.g., ethylene) may be a product of the ODH reactor system 100.

In some embodiments, the catalyst 110, 114, 118 in the reactors 102, 104, 106 (process sides 108, 112, 116) is different, respectively, and may give conversion of the alkane to the corresponding alkene at different temperatures, respectively. The first catalyst 110 may be different than the second catalyst 114 and the third catalyst 118, and the second catalyst 114 may be different than the third catalyst 118. In certain embodiments, the third reactor 106 reaction temperature is greater than the second reactor 104 reaction temperature, and the second reactor 104 reaction temperature is greater than the first reactor 102 reaction temperature.

The arrangement of the three ODH reactors 102, 104, 106 may be a once-through effluent/feed configuration in that the effluent 122 from the first ODH reactor 102 is feed to the second ODH reactor 104, and the effluent 124 from the second ODH reactor 104 is feed to the third ODH reactor 106. In certain embodiments, oxygen may be injected into the effluent 122 or the second ODH reactor 104 to supplement the effluent 122 with oxygen to account for consumption (depletion) of oxygen by the first ODH reactor 102. Likewise, oxygen may be injected into the effluent 124 or third ODH reactor 106 to supplement the effluent 124 with oxygen to account for depletion of oxygen by the second ODH reactor 104. Oxygen may also be fed directly to the second reactor 102 or the third reactor 104.

In some implementations, the ODH reactor system 100 may have a conduit to provide, if desired, feed (e.g., similar or same as feed 120) or fresh lower alkane (e.g., ethane) to the second ODH reactor 104 to supplement the effluent 122 received from the first ODH reactor 102. This additional feed or fresh alkane may be added to the effluent 122 or directly to the reactor 104. Similarly, the ODH reactor system 100 may have a conduit to provide feed (e.g., similar or same as feed 120) or fresh lower alkane to the third ODH reactor 106 to supplement the effluent 124 received from the second ODH reactor 104. This additional feed or fresh alkane may be added to the effluent 124 or directly to the reactor 106.

Moreover, any acetic acid in the effluent 122 from the first ODH reactor 102 may be oxidized into carbon dioxide in the second ODH reactor 104, depending on the operating temperature of the second ODH reactor 104. Any acetic acid in the effluent 124 from the second ODH reactor 104 may be combusted into carbon dioxide in the third ODH reactor 106, depending on the operating temperature of the third ODH reactor 106.

The first ODH reactor 102 has a jacket 128, the second ODH reactor 104 has a jacket 130, and the third ODH reactor 106 has a jacket 132. In this illustrated example of FIG. 1, the heat transfer fluid that flows through the jackets 128, 130, 132 is water (e.g., boiler feedwater). Also, in this example, the ODH reaction system 100 includes three flash vessels 134, 136, 138 for the generation of steam. A liquid level (water) may be maintained in the three flash vessels 134, 136, 138.

Water from a source 140 (e.g., a vessel) is supplied via a motive device 142 (e.g., pump) through conduits to the flash vessels 134, 136, 138. One or more control components, such as control valves 144, 146, 148, disposed along the respective conduits may maintain or adjust the amount of water conveyed to the flash vessels 134, 136, 138. The control valves 144, 146, 148 may maintain or modulate the volumetric flow rate or mass flow rate of the supplied water. The water may be demineralized water, steam condensate, or boiler feedwater, and the like.

Water from the flash vessels 134, 136, 138 as the heat transfer fluid may be provided through conduits to the ODH reactors 102, 104, and 106, respectively, to control temperature on the process side of the reactors. Water may circulate from the respective flash vessel 134, 136, 138 through the jacket 128, 130, 132. The motive force for the circulation may be by thermosiphon. In other examples, a motive device (e.g., pump) is disposed on each circulation loop to provide motive force (e.g., to pump) the water through the jacket.

The reaction temperature in the reactors 102, 104, 106, may depend on the type of catalyst. Thus, the temperature of the water flowing through the jackets 128, 130, 132 may be affected by the type of catalyst 110, 114, 118 on the process side of the reactors. Therefore, the pressure of the steam generated in the flash vessels 134, 136, 138 may be affected by the type of catalyst in the respective reactor.

For the first ODH reactor 102, water 150 from the first flash vessel 134 enters and flows through the first-reactor jacket 128 to acquire heat from the first-reactor process side 108. The heated water exits the jacket 128 as return water 152 to the flash vessel 134. The heat acquired by the water promotes flashing of liquid water into steam in the flash vessel 134. Steam 154 discharges overhead from the flash vessel 134 (e.g., into a conduit). The steam 154 may be a coproduct of the ODH reactor system 100.

The pressure of the steam 154 may depend on the catalyst 110 in first ODH reactor 102. In other words, the reaction temperature driven by the catalyst 110 generally affects the temperature of the return water 152 discharging from the jacket 128 to the flash vessel 134. The temperature of the return water 152 may affect the pressure at which the liquid water flashes into the steam 154 discharging from the flash vessel 134. In examples, the steam 154 may generally be saturated steam. In certain implementations, the catalyst 110 in the first reactor 102 provides for a reaction temperature of less than 400° C. The steam 154 may be, for example, low pressure steam at less than 150 psig or medium pressure steam in the pressure range of 150 psig to 600 psig. The pressure may generally define the temperature of the steam 154. The temperature and enthalpy of the return water 152 may limit the pressure at which flashing can occur in the flash vessel 134. Moreover, the amount (and pressure) of steam 154 may be correlative to the first reactor duty (heat generated) removed via heat of vaporization of the flashing water in the flash vessel 134. The duty or amount of heat generated by the first ODH reactor 102 may be related to the catalyst 110 employed in the first reactor 102 and to the production rate of the corresponding alkene in the first reactor 102, and so on. In some embodiments, the steam 154 may be routed through a heat exchanger (e.g., shell-and-tube heat exchanger) to heat the steam 154 to above saturation temperature. In one embodiment, a portion of the return water 152 is diverted from entry to the flash vessel 134 and is utilized as a heating medium in the heat exchanger to heat the steam 154 above saturation temperature. Other sources of a heating medium (heat transfer fluid) are applicable for the heat exchanger. Lastly, the pressure of the flash vessel 134 (and similar flash vessels in FIGS. 1-8) may be controlled by the downstream backpressure of the steam header or user, by a control valve on the steam discharge conduit from the overhead of the flash vessel, and/or by the amount of makeup water (e.g., water 140) fed to the flash vessel, and so on.

For the second ODH reactor 104, water 156 discharges from a bottom portion of the second flash vessel 136 and flows through the second-reactor jacket 130 to receive heat from the process side 112 of the second ODH reactor 104. The heated water exits the jacket 130 as return water 158 to the flash vessel 136. The heat acquired by the water promotes flashing of liquid water into steam in the second flash vessel 136. Steam 160 discharges overhead from the second flash vessel 136. The steam 160 may be a coproduct of the ODH reactor system 100.

The pressure of the steam 160 may depend on the catalyst 114 in the second ODH reactor 104. The reaction temperature driven by the catalyst 114 in the second ODH reactor 104 generally affects the temperature of the return water 158 discharging from the jacket 130 to the flash vessel 136. The temperature of the return water 158 may affect the pressure at which the liquid water flashes into the steam 160 discharging from the second flash vessel 136. Moreover, the amount (and pressure) of the steam 160 may be related to the heat generated by the reaction in the second ODH reactor 104, and removed via heat of vaporization of the flashing water in the second flash vessel 136. The amount of heat generated by the second ODH reactor 104 may be related to the catalyst 114 employed in the second reactor 104 and to the amount (rate) of alkane converted to alkene in the second reactor 104, and the like.

In examples, the steam 160 may generally be saturated steam. In certain implementations, the catalyst 114 in the second reactor 104 provides for a reaction temperature of greater than 400° C. (e.g., in the range of 400° C. to 500° C.). In those implementations, the steam 160 exiting overhead from the second flash vessel 136 may be, for example, medium pressure steam in the range of 150 psig to 600 psig or in the range of 250 psig to 400 psig, or high pressure steam in the pressure range of 600 psig to 1500 psig. The catalyst 114 providing for a reaction temperature in the range of 400° C. to 500° C. may lead to steam 160 as medium pressure steam but can also give or result in the steam 160 as high pressure steam at 600 psig or greater, depending on reactor operating conditions and other factors. The pressure generally defines the temperature of the steam 160. The steam 160 may be at saturation temperature. In some embodiments, the steam 160 may be routed through a heat exchanger (e.g., shell-and-tube heat exchanger) to heat the steam 160 to above saturation temperature. Thus, in certain implementations, the steam 160 is superheated high-pressure steam. In examples, a heat transfer fluid providing heat in the heat exchanger that superheats the steam 160 is the effluent 126 from the third ODH reactor 106 routed through the heat exchanger.

For the third ODH reactor 106, water 162 flows from the bottom portion of the third flash vessel 138 through the third-reactor jacket 132 to accumulate heat from the process side 116 of the third ODH reactor 106. The heated water exits the jacket 132 as return water 164 to the third flash vessel 138. The heat acquired by the water promotes flashing of liquid water into steam in the third flash vessel 138. Steam 166 exits from an upper portion of the third flash vessel 138 into a conduit for distribution. The steam 166 may be a coproduct of the ODH reactor system 100.

The pressure of the steam 166 may depend on the catalyst in third ODH reactor 106. The reaction temperature associated with the catalyst 118 in the third ODH reactor 106 may drive the temperature of the return water 164 discharging from the jacket 132 to the flash vessel 138. The temperature of the return water 164 may determine the pressure at which the liquid water flashes into the steam 166 discharging from the flash vessel 138.

In examples, the steam 166 may generally be saturated steam. The steam 166 may be subjected to further processing (e.g., heating) to superheat the steam 166. In certain embodiments, the catalyst 118 in the third ODH reactor 106 provides for a reaction temperature at 500° C. or greater, and the steam 160 is high pressure steam at 600 psig or greater or very high pressure steam at 1500 psig or greater.

The amount (and pressure) of the steam 166 generated may be correlative with the heat generated in the third ODH reactor 106 and removed by the jacket water for temperature control of the third reactor 106. The removed heat may give the heat of vaporization for the flashing water in the third flash vessel 138. The amount of heat generated by the third ODH reactor 108 may be related to the catalyst 116 employed in the third reactor 104, the amount (rate) of unreacted alkane converted to the corresponding alkene in the third ODH reactor 106, and so forth.

Figure 2:
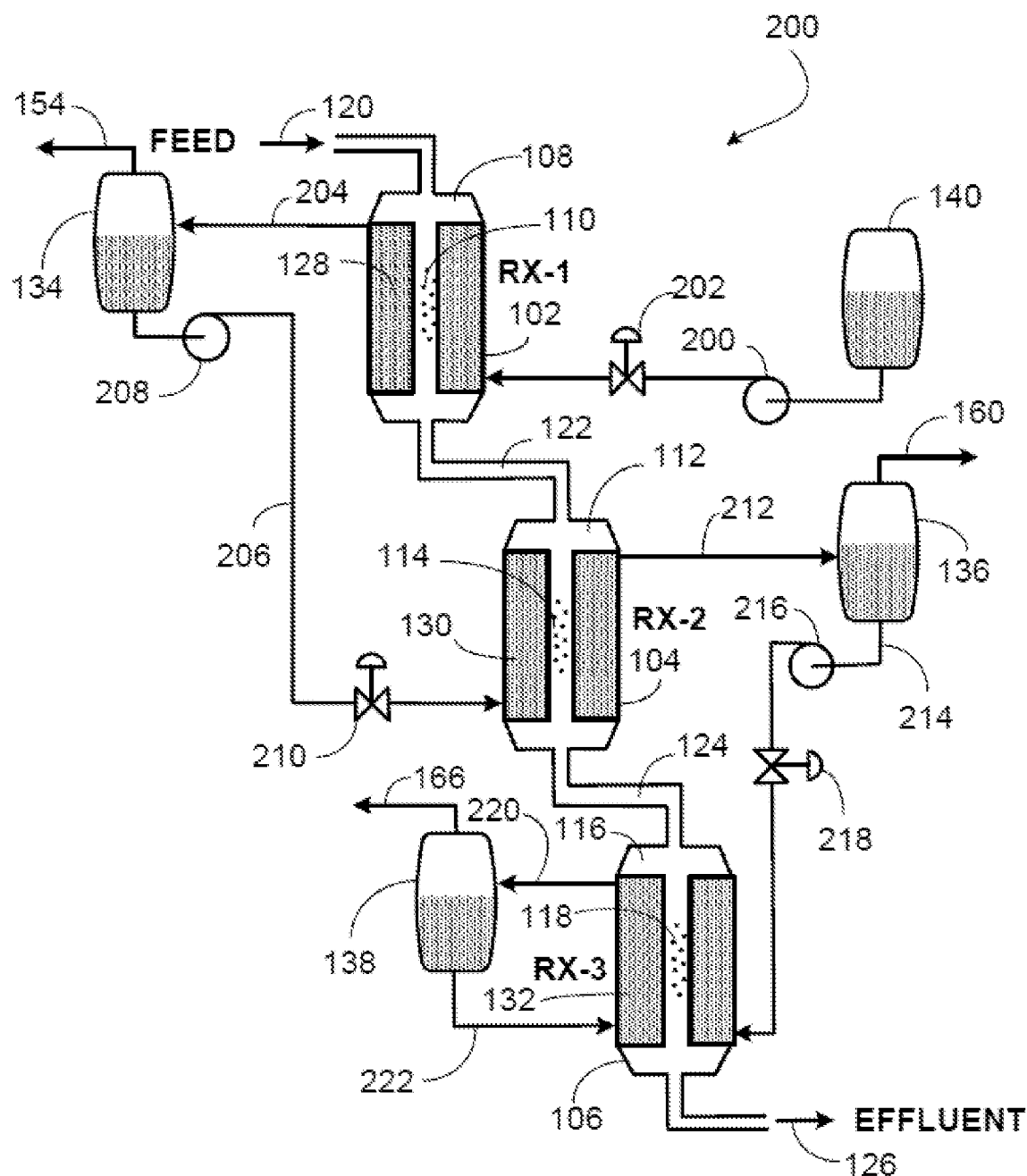

FIG. 2 is an ODH reactor system 200 having the three ODH reactors 102, 104, 106 discussed above with respect to FIG. 1. The system 200 receives the feed 120 having an alkane (e.g., ethane). The first ODH reactor 102 discharges an effluent 122 having a corresponding alkene and unreacted alkane to the second ODH reactor. The first ODH reactor 102 provides both (1) catalytic conversion and (2) the effluent 122 as a preheated feed to the second ODH reactor 104. The second ODH reactor 104 discharges an effluent 124 having the corresponding alkene and unreacted alkane to the third ODH reactor 106. The second ODH reactor 104 provides for both (1) catalytic conversion and (2) the effluent 124 as a preheated feed to the third ODH reactor 106. The third ODH reactor 106 discharges an effluent 126 having the corresponding alkene and any unreacted alkane. The corresponding alkene (e.g., ethylene) in the third-reactor effluent 126 may be a product of the ODH reactor system 200.

In system 200, the routing of water as the heat transfer fluid is different than in the system 100 of FIG. 1. The system 200 has the flash vessels 134, 136, 138, which may be the same or similar to those depicted in FIG. 1. However, the flash vessels 134, 136, 138 receive input water from the respective reactor jacket instead of directly from the water source 140. A cascade flow of water is employed. In other words, the second-reactor jacket 130 receives water from the first flash vessel 134. Thus, some heat from the first ODH reactor 102 system may be utilized by the second ODH reactor 104 system. The third-reactor jacket 132 receives water from the second flash vessel 136. Thus, some heat from the first ODH reactor 102 system and the second ODH reactor 104 system may be utilized by the third ODH reactor 106 system. The mass flow rates of the coproduct steam streams 154, 160, 166 may be affected by the alternative flows of the jacket water shown in FIG. 2 as compared to FIG. 1.

For the first ODH reactor 102, water is conveyed from the water source 140 to the first-reactor jacket 128 to control temperature of the first-reactor process side 108. In the illustrated embodiment, a pump 200 (e.g., centrifugal pump) provides motive force for flow of the water. For temperature control of the first reactor 102, the flow rate of the water may be maintained or modulated via a control valve 202 disposed on the conduit conveying the water. The water flowing through the first-reactor jacket 128 acquires heat from the first-reactor process side 108 and discharges from the jacket 128 as heated water 204 to the first flash vessel 134. In implementations, the set point of the control valve 202 may be specified in response to the temperature of the process side 108 or the temperature of the heated water 204, or both. The heat acquired by the water promotes flashing of liquid water into steam in the first flash vessel 134.

Steam 154 discharges overhead from the first flash vessel 134 into a conduit for distribution. The steam 154 may be a coproduct of the ODH reactor system 200. The pressure of the steam 154 may depend on the catalyst 110 in first ODH reactor 102, as discussed. In one example, the pressure of the steam 154 is low pressure steam at 150 psig or less. The temperature of the heated water 204 (and the amount of heat acquired from the first ODH reactor 102) may determine the pressure at which the liquid water flashes into the steam 154 discharging from the flash vessel 134. The amount of heat acquired by the jacket water may be the heat generated by the first ODH reactor 102 in the ODH catalytic conversion reaction in the first ODH reactor 102.

For the second ODH reactor 104, water 206 discharges from a bottom portion of the first flash vessel 134 to the second-reactor jacket 130. The water 206 may be conveyed via a pump 208 (e.g., centrifugal pump). For temperature control of the second reactor 104, a control valve 210 may control the flow rate of the water 206. The water 206 flows through the second-reactor jacket 130 and acquires heat from the second-reactor process side 112. The heated water 212 exits the jacket 130 to the second flash vessel 136. The set point of the control valve 202 may be set in response to the temperature of the process side 112 or the temperature of the heated water 212, or both. The heat acquired by the water promotes flashing of liquid water into steam in the second flash vessel 136.

Steam 160 discharges overhead from the second flash vessel 136 to be conveyed to users of the steam 160. The steam 160 may be a coproduct of the ODH reactor system 200. The pressure of the steam 160 may depend on the catalyst 114 in the second ODH reactor 104, as discussed. In one example, the pressure of the steam 160 is medium pressure steam in the range of 150 psig to 600 psig. In another example, the pressure of the steam 160 is high pressure steam at 600 psig or greater.

The temperature of the heated water 212 (and the amount of heat acquired from the second ODH reactor 104) may determine the pressure at which the liquid water flashes into the steam 160 discharging from the flash vessel 136. The amount of heat acquired in the heated stream 212 may be at least the heat generated by the second ODH reactor 104 in the ODH catalytic conversion reaction in the second ODH reactor 104. The heated water 212 may also contain heat from the first ODH reactor 102 system.

For the third ODH reactor 106, water 214 flows from the bottom portion of the second flash vessel 136 through the third-reactor jacket 132 to receive heat from the third-reactor process side 116. The water 214 may be transported via a pump 216 and a control valve 218. The flow of water 214 through the jacket 132 as a heat transfer fluid (jacket water) is for temperature control of the third ODH reactor 106. The heated water 220 exits the jacket 132 to the third flash vessel 138. Optionally, water 222 as additional jacket water may flow by thermosiphon from a bottom discharge of the flash vessel 138 to the jacket 132. The heat acquired by the jacket water promotes flashing of liquid water into steam in the flash vessel 138.

Steam 166 exits from an upper portion of the third flash vessel 138 into a conduit. The steam 166 may be a coproduct of the ODH reactor system 200. The pressure of the steam 166 may depend on the catalyst 118 in third ODH reactor 106, as discussed. In one example, the pressure of the steam 166 is high pressure steam at 600 psig or greater. The temperature of the heated water 220 (and the amount of heat acquired from the third ODH reactor 106) may determine the pressure at which the liquid water flashes into the steam 166 discharging from the flash vessel 138. The amount of heat acquired in the heated stream 220 may be at least the heat generated by the third ODH reactor 106 in the ODH catalytic conversion reaction in the third ODH reactor 106. The heated water 220 may also contain heat from the first ODH reactor 102 system and the second ODH reactor 104 system.

Figure 3:
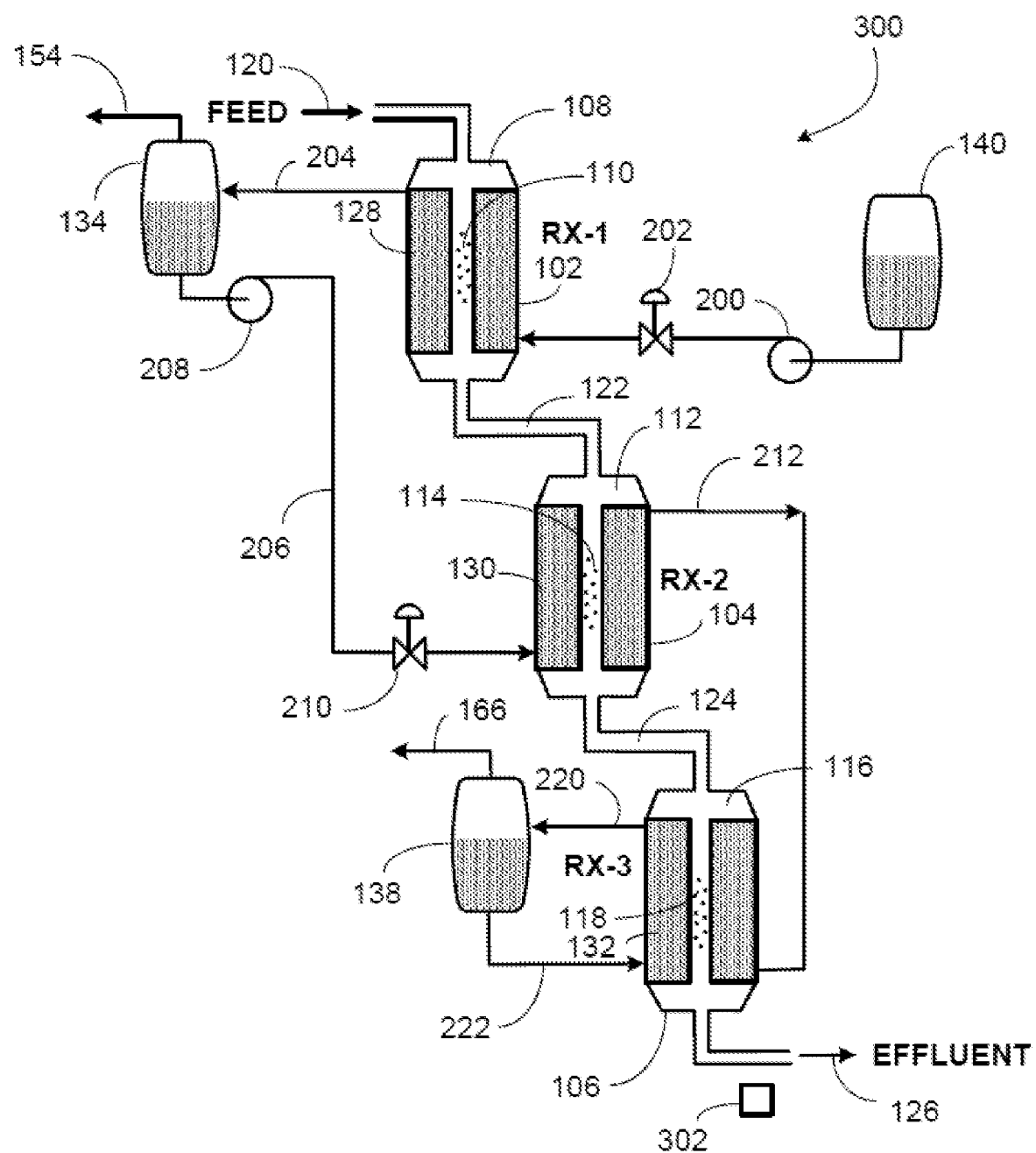

FIG. 3 is an ODH reactor system 300 having the three ODH reactors 102, 104, 106 discussed above. The first ODH reactor 102 performs as a catalytic conversion reactor and also serves as a feed preheater for the second ODH reactor 104. The second ODH reactor 104 performs as a catalytic conversion reactor and also serves as a feed preheater for the third ODH reactor 106.

Each reactor 102, 104, 106 may be a reactor vessel having an inlet and an outlet. The inlet may be to a process side of the reactor and the outlet may be from a process side of the reactor. The inlet may be for feed including a hydrocarbon (and oxygen) and the outlet for an effluent including hydrocarbon. The reactor vessel may have a jacket for heat transfer fluid. The jacket may have a jacket inlet to receive heat transfer fluid and a jacket outlet to discharge heat transfer fluid.

The ODH reactor system 300 is similar to the ODH reactor system 200 of FIG. 2, except that the system 300 does not include the second flash vessel 136 or the associated steam 160 as coproduct stream. The third flash vessel 138 becomes the second flash vessel in FIG. 3. The amount of the coproduct steam 166 generated may be increased. As for the jacket water flow, the heated water 212 that discharges from the second-reactor jacket 130 flows to the third-reactor jacket 132. The upstream pump 208 and control valve 210 may be sized accordingly. The control valve 210 may be tuned for temperature control of both the second ODH reactor 104 and the third ODH reactor 106. The optional thermosiphon flow of water 222 from the flash vessel 138 to the jacket 132 may further facilitate the temperature control in the third reactor 106.

The coproduct steam 166 discharged overhead from the flash vessel 138 may be heated downstream to superheat the steam 166. Therefore, the coproduct steam 166 may be superheated steam. In some implementations, the steam 166 may be heated in a heat exchanger 302 (e.g., cross exchanger, shell-and-tube heat exchanger, etc.) by the third-reactor effluent 126. In one example, the steam 166 is superheated high-pressure steam at 600 psig or greater.

Figure 4:
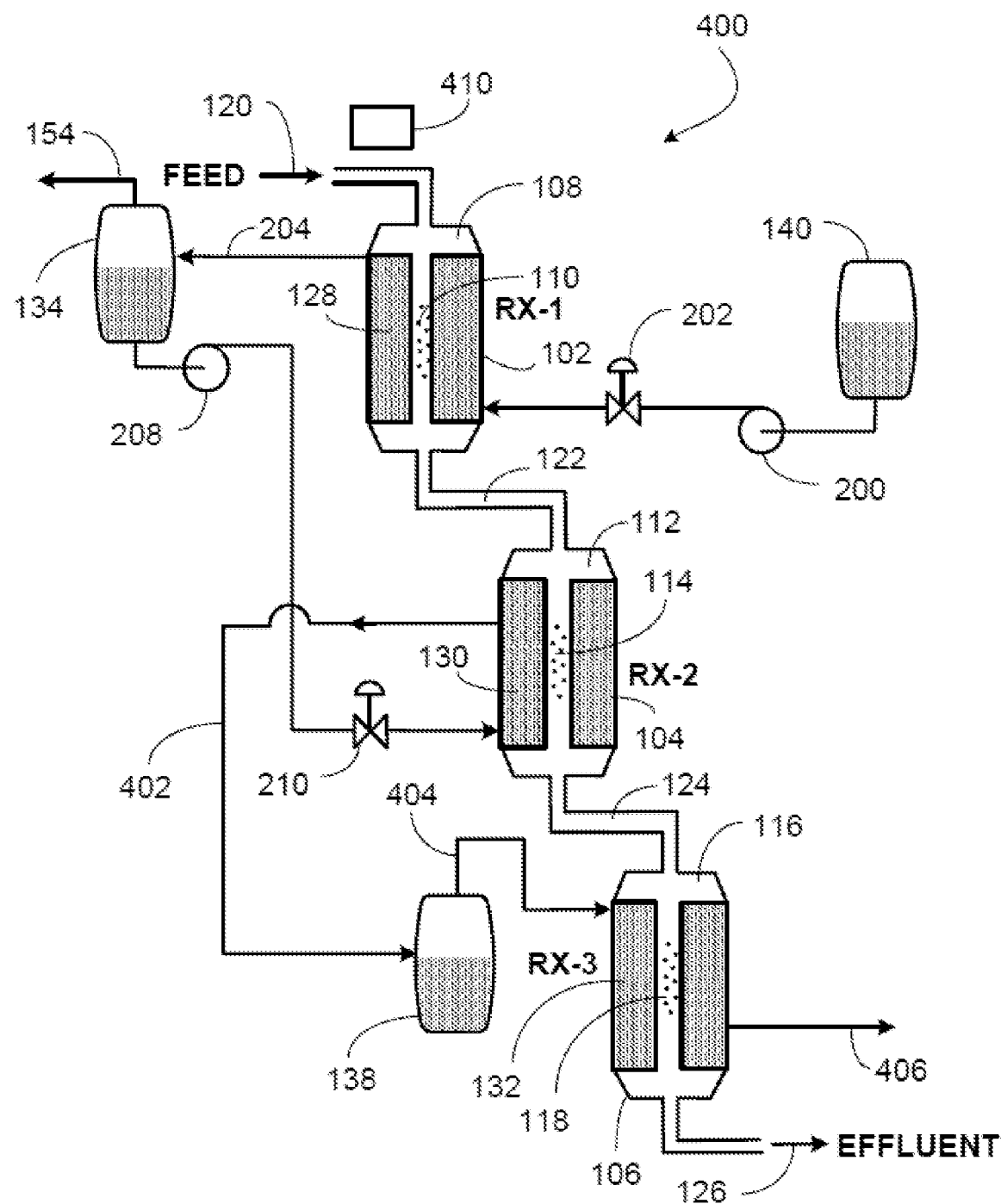

FIG. 4 is an ODH reactor system 400 having the three ODH reactors 102, 104, 106 discussed above. The system 400 is similar to the ODH reactor system 300 of FIG. 3, except that steam (with little or no liquid water) is flowed through the third-reactor jacket 132 as heat transfer fluid.

The heated water 402 from the second-reactor jacket 130 is routed to the flash vessel 138. The heated water 402 may be liquid water or steam, or a mixture (two-phase flow) of steam and liquid water. For service as a heat transfer fluid, steam 404 discharges from an upper portion of the flash vessel 138 through a conduit to the third-reactor jacket 132. In examples, the steam 404 may be high pressure steam (600 psig or greater) or very high pressure steam (1500 psig or greater). Heated steam exits the third-reactor jacket 132 into a conduit as coproduct superheated steam 406 for distribution to users.

A control valve (not shown) may modulate and control the flow rate (e.g., mass per time) of the steam 404 flowing through the jacket 132 for the temperature control of the third-reactor process side 116. The control valve (if employed) may be disposed on the jacket 132 discharge conduit or on the inlet conduit upstream of the jacket 132. The steam 406 may be superheated high pressure steam or superheated very high pressure steam.

Lastly, in certain embodiments, the feed 120 to the first ODH reactor 102 may be heated (preheated) prior to entry into the first ODH reactor 102. For example, the feed 120 may be routed through a heat exchanger 410 (e.g., cross exchanger, shell-and-tube heat exchanger, etc.) and heated by the third-reactor effluent 126 routed through the heat exchanger 410.

Figure 5:
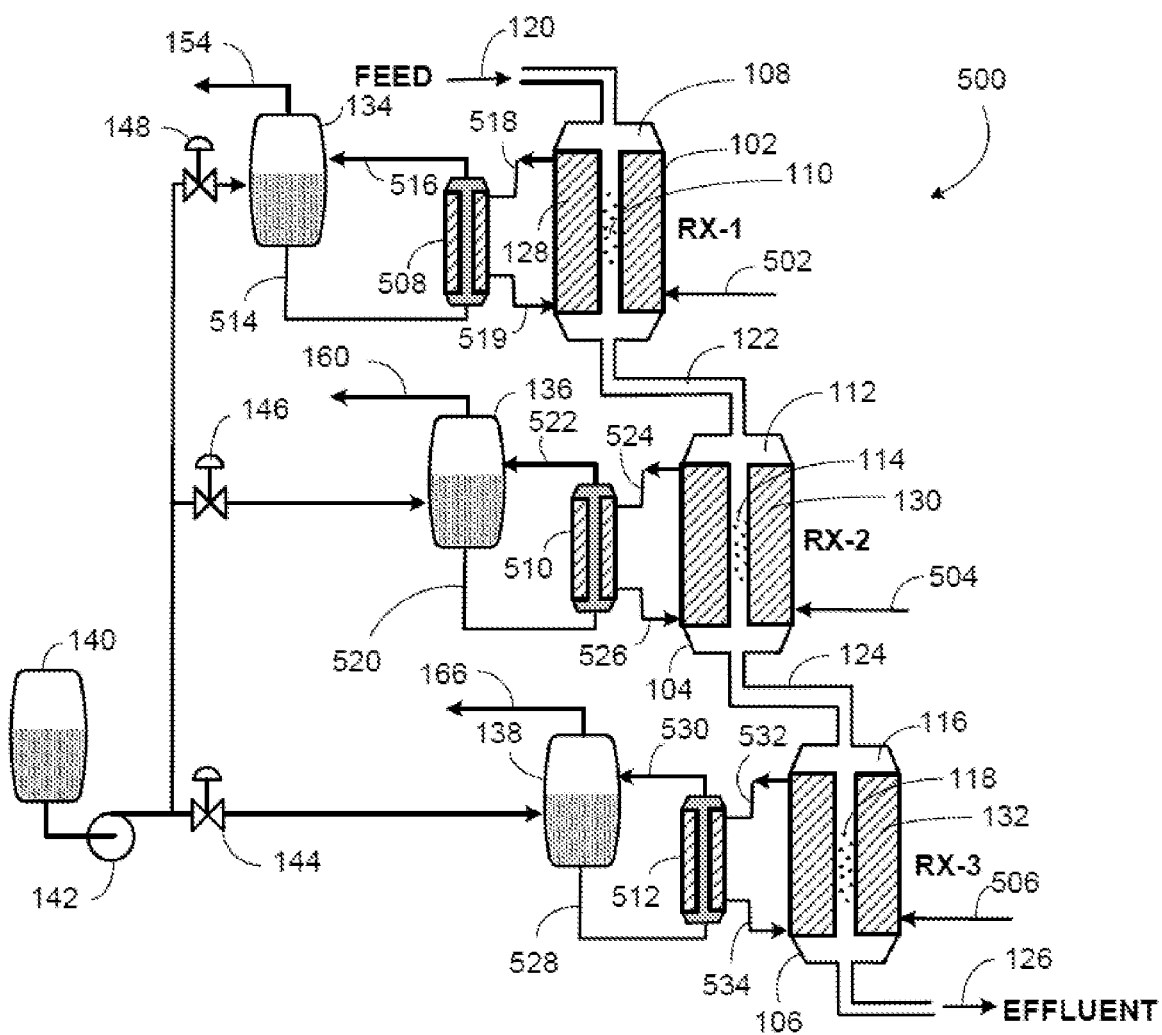

FIG. 5 is an ODH reactor system 500 having three reactors that are the same or similar as the three ODH reactors 102, 104, 106 discussed above. In implementations, the three ODH reactors 102, 104, 106 may be fabricated with a heat transfer area (between the process side and jacket) specified based on various factors. Such factors may include the heat transfer fluid that will be utilized, the amount of heat that will be generated by the reactor, the flow rate of the heat transfer fluid through the jacket, and so forth. For the system 500 in operation, FIG. 5 depicts the liquid water with gray shading and the heat transfer fluid with forward slashed lines. Such indications are retained in FIGS. 6-8.

In the illustrated embodiment of FIG. 5, the heat transfer fluid 502, 504, 506 introduced to the respective reactor jackets 128, 130, 132 may be treated water (e.g., demineralized water, boiler feedwater, etc.), glycol (e.g., ethylene glycol, propylene glycol, etc.), molten salt, or other type of heat transfer fluid. In embodiments with the heat transfer fluid 502, 504, 506 as molten salt, three molten-salt supply systems may be employed to provide molten salt as the heat transfer fluid 502, 504, and 506, respectively.

Examples of the heat transfer fluid include DOW-THERM™ heat transfer fluids (Dow Chemical Company, Midland, Michigan USA), which may have glycol or synthetic organic compounds generally. Examples of the heat transfer fluid may include DW-Therm HT products (Huber USA, Gary, North Carolina USA), Syltherm™ silicon fluids (e.g., Syltherm™ 800) (Dow Chemical Company, Midland, Michigan USA), and Santolube products (e.g., OS-750™ or OS-124™) (SantoLubes LLC, Spartanburg, South Carolina USA). Of course, temperature limitations on these various organic heat-transfer fluids are taken into account.

In certain embodiments, each reactor 102, 104, 106 is associated with a heat exchanger 508, 510, 512 (e.g., shell-and-tube heat exchanger, plate and frame heat exchanger, etc.) that heats water with the heat transfer fluid discharged from the reactor jacket. The water to be heated is pumped via a pump 142 from a water source 140 to the three flash vessels 134, 136, 138. Control valves 144, 146, 148 may be disposed on the conduits conveying the water to modulate the respective flow rate of the water to the flash vessels 134, 136, 138. In embodiments, this water is boiler feedwater. The water is heated in the heat exchanger 508, 510, 512 with the heat transfer fluid (discharged from the reactor jacket) so to flash the water into steam in the flash vessel 134, 136, 138 to generate steam.

For the first ODH reactor 102, water 514 discharges from a bottom portion of the first flash vessel 134 and is heated in the first heat exchanger 508. The heated water discharges from the heat exchanger 508 as return water 516 to the first flash vessel 134. This circulatory flow of the water through the heat exchanger 508 may be by thermosiphon.

Liquid water in the first flash vessel 134 flashes into steam 154 that discharges from the first flash vessel 134 as coproduct steam. The conditions (e.g., amount, pressure, temperature, etc.) of the steam 154 may depend on the catalyst 110 type in the first ODH reactor 102, the operating (reaction) temperature of the first ODH reactor 102, the amount of heat generated by the first ODH reactor 102, and other factors.

The heat transfer fluid 502 is heated in the first-reactor jacket 128 and discharges as heated heat-transfer fluid 518 to the first heat exchanger 508. In the first heat exchanger 508, heat transfer occurs from the heated heat-transfer fluid 518 to the water 514. The heat transfer fluid discharges from the heat exchanger 508 as cooled heat-transfer fluid 519 to the reactor jacket 128. In certain implementations, some or all of the cooled heat-transfer fluid 519 may be returned to the heat-transfer fluid supply system instead of returned to the jacket 128.

Moreover, a flow bypass conduit may be provided around the heat exchanger 508. Thus, a first portion of the heated heat-transfer fluid 518 may flow through the heat exchanger 508. A second portion of the heated heat-transfer fluid 518 bypasses (flows around) the heat exchanger 508 through the flow bypass conduit. In examples, the first portion and second portion may each be in the range of 20 weight percent to 80 weight percent of the heated heat-transfer fluid 518.

For the second ODH reactor 104, the operation of steam generation may be similar as with the first ODH reactor 102 but with the option to generate steam at different pressure. A different pressure steam may be produced, for example, by utilizing a catalyst 114 in the second ODH reactor 104 that is different than the catalyst 110 in the first ODH reactor 102.

In the steam generation for the second ODH reactor 104, water 520 discharges from a bottom outlet of the second flash vessel 136 and is heated in the second heat exchanger 510. The heated water exits the heat exchanger 510 as return water 522 to the second flash vessel 134. The motive force for this circulation of water through the second-reactor jacket 130 may be by thermosiphon. Liquid water in the second flash vessel 136 vaporizes into steam 160. The steam 160 may exit overhead from the second flash vessel 136 as coproduct steam. The amount, pressure, and temperature of the steam 160 may depend on the catalyst 114 type in the second ODH reactor 104, the operating (reaction) temperature of the second ODH reactor 104, the amount of heat generated by the second ODH reactor 104, and so forth.

The heat transfer fluid 504 is heated in the second-reactor jacket 130 and discharges as heated heat-transfer fluid 524 from the jacket 130 to flow through the second heat exchanger 510. Heat transfer occurs from the heated heat-transfer fluid 524 to the water 520. The heat transfer fluid discharges from the heat exchanger 510 as cooled heat-transfer fluid 526 to the reactor jacket 130. In certain implementations, some or all of the cooled heat-transfer fluid 526 may be returned to the heat-transfer fluid supply system instead of to the jacket 130. Also, in some embodiments, a portion of the heated heat-transfer fluid 524 may flow around the heat exchanger 510 via a flow bypass conduit in parallel with the heat exchanger 510. In examples, the portion routed through the bypass may be at least 20 weight percent of the heated heat-transfer fluid 524, at least 50 weight percent of the heated heat-transfer fluid 524, or at least 75 weight percent of the heated heat-transfer fluid 524.

For the third ODH reactor 106, the operation of steam generation may be similar as with the first ODH reactor 102 and the second ODH reactor 104 but with the option to generate steam at different pressure. A different pressure steam may be generated, for instance, by utilizing a catalyst 118 in the third ODH reactor 106 that is different than the catalyst 110 in the first ODH reactor 102 and different than the catalyst 114 in the second ODH reactor 104.

To produce steam with the third ODH reactor 106, water 528 discharges from a bottom outlet of the third flash vessel 138 and is heated in the third heat exchanger 512. The heated water exits the heat exchanger 512 as return water 530 to the third flash vessel 138 via thermosiphon in this example. Liquid water in the third flash vessel 138 vaporizes into steam 166, which may discharge from an upper portion of the third flash vessel 138 as coproduct steam. The amount, pressure, and temperature of the steam 160 may be correlative with a number of factors. For example, the factors may include the third-reactor catalyst 118 type, the reaction temperature on the third-reactor process side 116, and the amount of heat generated by the reaction on the process side 116.

The heat transfer fluid 506 is heated in the third-reactor jacket 132 and discharges as heated heat-transfer fluid 532 to the third heat exchanger 512. Heat transfer occurs from the heated heat-transfer fluid 432 to the water 528 in the third heat exchanger 512. The heat transfer fluid discharges from the heat exchanger 512 as cooled heat-transfer fluid 534 to the reactor jacket 132. Some or all of the cooled heat-transfer fluid 534 may return to the heat-transfer fluid supply system instead of sent to the jacket 132. Moreover, in embodiments, a portion of the heated heat-transfer fluid 532 may flow through a conduit to bypass the heat exchanger 512.

Figure 6:
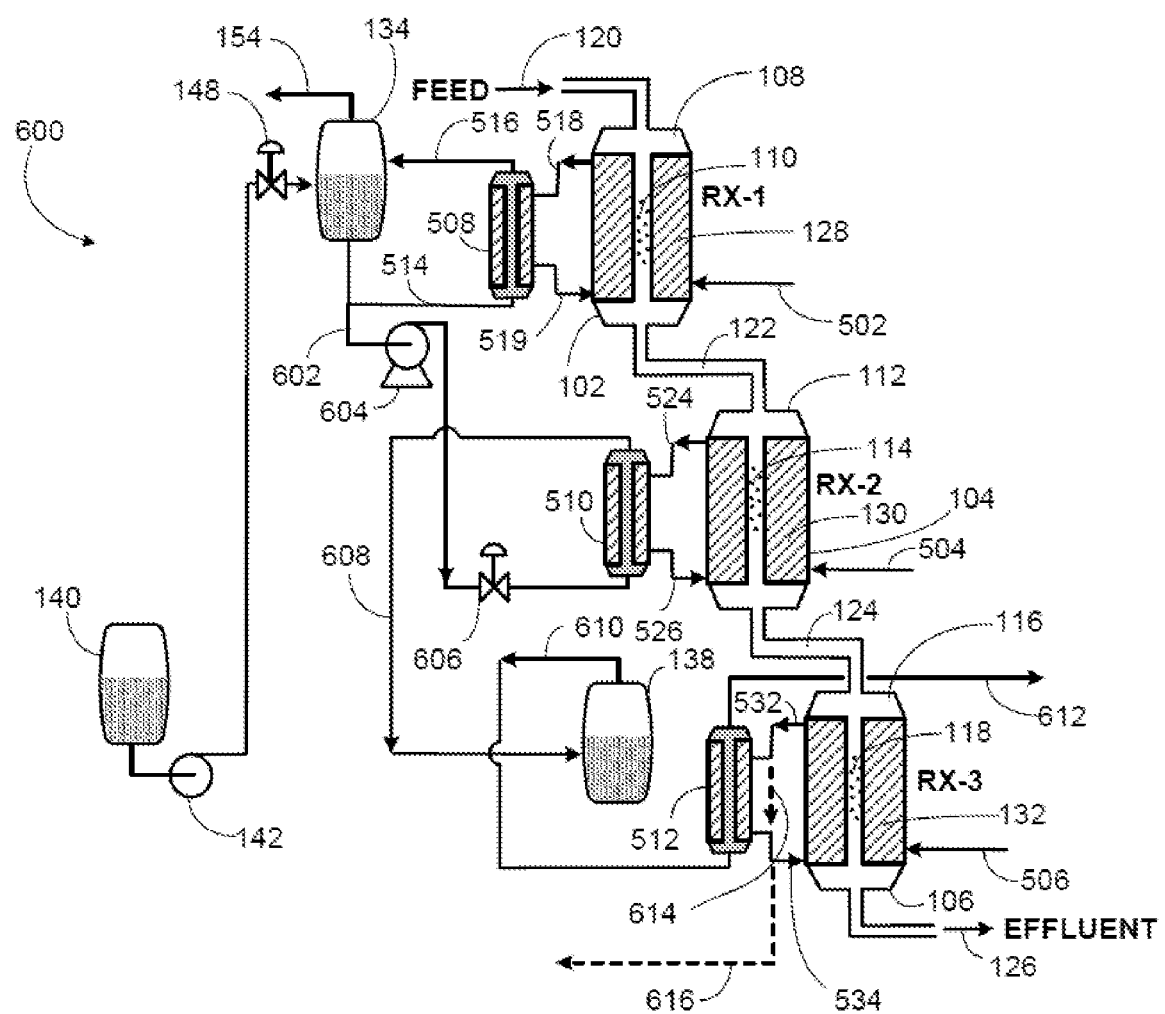

FIG. 6 is an ODH reactor system 600 having three reactors the same or similar as the three ODH reactors 102, 104, 106 discussed above. The three ODH reactors 102, 104, 106 have a first catalyst 110, a second catalyst 114, and a third catalyst 118, respectively. The first catalyst 110, second catalyst 114, and third catalyst 118 may each be a fixed bed of catalyst and be different or same catalyst type with respect to each other.

The system 600 receives the feed 120 having an alkane (e.g., ethane). The first ODH reactor 102 discharges an effluent 122 having a corresponding alkene and unreacted alkane. The second ODH reactor 104 receives the first-reactor effluent 122 and discharges an effluent 124 having more corresponding alkene (and less unreacted alkane) than the first-reactor effluent 122. The third ODH reactor 106 receives the second-reactor effluent 124 and discharges an effluent 126 having the corresponding alkene and any remaining unreacted alkane. The corresponding alkene (e.g., ethylene) in the third-reactor effluent 126 may be a product of the ODH reactor system 600.

The system 600 utilizes a heat transfer fluid as discussed with respect to FIG. 5. However, in comparison to the system 500, aspects of the steam generation are altered in system 600, as indicated below. For instance, in the example of FIG. 6, the second flash vessel 136 is not employed.

For system 600, the water (e.g., boiler feedwater) to be heated to generate steam is pumped from the water source 140 via the pump 142 to the first flash vessel 134. The control valve 148 disposed along the conduit conveying the water may maintain or adjust the flow rate of the water to the first flash vessel 134. Water is fed from the first flash vessel 134 to both the first heat exchanger 508 (associated with the first ODH reactor 102) and the second heat exchanger 510 (associated with the second ODH reactor 104). Water 514 is fed from the first flash vessel 134 to the first heat exchanger 508 by thermosiphon. Water 602 is fed from the first flash vessel 134 to the second heat exchanger 510 via a pump 604. A control valve 606 disposed along the conduit conveying the water 602 may maintain or adjust the flow rate of the water 602 through the second heat exchanger 510. The flow rate of water 602 through the second heat exchanger 510 may be modulated by the control valve 606 for temperature control of the second reactor 104.

The water 514 in the first heat exchanger 508 is heated with the heated heat-transfer fluid 518 from the first reactor jacket 128. Thus, in this reactor temperature control, the water 514 receives the heat generated by the first-reactor 102 reaction. The heated water discharges from the first heat exchanger 508 as return water 516 to the first flash vessel 134. Liquid water in the first flash vessel 134 flashes into steam 154 that exits overhead from the first flash vessel 134 as coproduct steam. In some examples, the steam 154 is saturated low-pressure steam at 150 psig or less.

The water 602 in the second heat exchanger 510 is heated with the heated heat-transfer fluid 524 from the second reactor jacket 130. In other words, for reactor temperature control, the water 602 receives the heat generated by the second-reactor 104 reaction. The heated water 608 discharges from the second heat exchanger 510 to the flash vessel 138. The heated water 608 flowing through the conduit to the flash vessel 138 may be liquid water or steam, or a mixture thereof (two-phase flow).

Steam 610 discharges from an overhead outlet of the flash vessel 138 is routed through the third heat exchanger 512 for temperature control of the third ODH reactor 106. The steam 610 is heated in the third heat exchanger 512 with the heated heat-transfer fluid 532 from the third-reactor jacket 132. The pressure of the steam 610 may be different than the pressure of the steam 154 discharged from the first flash vessel 134. The pressure may be different due at least in part to utilizing a catalyst 114 in the second ODH reactor 104 and a catalyst 118 in the third ODH reactor 106 that are different than the catalyst 110 in the first ODH reactor 102. In implementations, the flow rate of the steam 610 through the heat exchanger 512 may be modulated by a control valve (not shown) for temperature control of the third reactor 106.

The heated steam discharges from the third heat exchanger 512 as superheated steam 612, which may be a coproduct of the ODH reactor system 600. In implementations, a control valve (not shown) may modulate the flow of the steam 610 (or steam 612) to control the temperature of the third reactor 106. In some examples, the superheated steam 612 is high pressure steam at 600 psig or greater, or very high pressure steam at 1500 psig or greater. In implementations, temperature of the steam 612 is at least 150° C. above the saturation temperature, or at least 200° C. above the saturation temperature. In one example, the superheated steam 612 has a pressure of about 1500 psig and a temperature of at least 500° C. or at least 510° C. In another example, the superheated steam 612 has a pressure of about 2000 psig and a temperature of at least 530° C. or at least 540° C.

Referring to FIG. 5 and FIG. 6, a portion of each of the heated heat-transfer fluids 518, 524, 532 that discharge from a reactor jacket may bypass the respective heat exchangers 508, 510, 512. See, for example, the dashed line 614 in FIG. 6. Moreover, a portion of each of the cooled heat-transfer fluids 519, 526, 534 discharging from the respective heat exchangers 508, 510, 512 may be returned to the heat-transfer fluid supply system instead of sent to the reactor jacket. See, for example, the dashed line 616 in FIG. 6.

The heat-transfer fluid supply system(s) that provides the heat transfer fluid 502, 504, 506 may have a heat exchanger (s) for temporary operation to heat the heat transfer fluid 502, 504, 506 supply. The heat exchanger may be put into operation when the three reactors 102, 104, 106 are not performing the catalytic reaction of alkane to alkene and thus are not generating heat. This temporary operation of the heat exchanger may therefore provide heat for steam generation in the ODH reactor system 500, 600.

Figure 7:
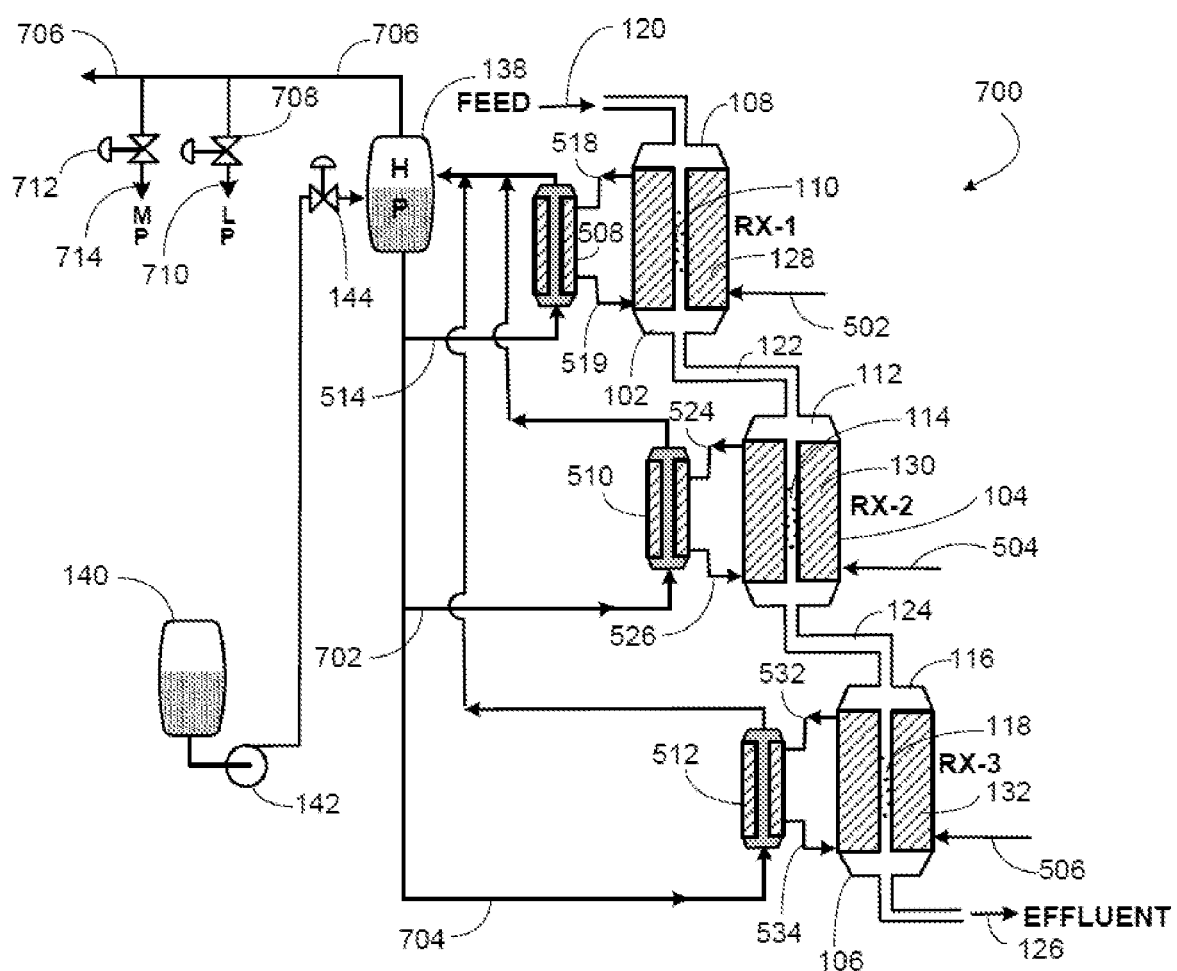

FIG. 7 is an ODH reactor system 700 having the three ODH reactors 102, 104, 106 in series each having a catalyst 110, 114, 118. As with the preceding figures, the system 700 receives the feed 120 having an alkane (e.g., ethane). The first ODH reactor 102 converts (via catalyst 110) some of the alkane to a corresponding alkene (e.g., ethylene). The first ODH reactor 102 discharges an effluent 122 having the corresponding alkene and unreacted alkane to the second ODH reactor 104. The second ODH reactor 104 converts (via catalyst 114) some of the unreacted alkane to the corresponding alkene. The second ODH reactor 104 discharges an effluent 124 having the corresponding alkene and unreacted alkane to the third ODH reactor 106. The third ODH reactor 106 converts (via catalyst 118) some unreacted alkane to the corresponding alkene. The third ODH reactor 106 discharges an effluent 126 having the corresponding alkene and any unreacted alkane. The corresponding alkene in the third-reactor effluent 126 may be a product of the ODH reactor system 700.

The system 700 includes the three heat exchangers 508, 510, 512 associated with the three ODH reactors 102, 104, 106. The three heat exchangers 508, 510, 512 may be the same or similar as in FIGS. 5 and 6. The three heat exchangers 508, 510, 512 may be configured differently than in FIGS. 5 and 6 because of the different arrangement for source of water flow through the heat exchangers 508, 510, 512.

Heat transfer fluid 502 is supplied to the first-reactor jacket 128. In the jacket 128, the heat transfer fluid 502 receives the heat generated by the ODH catalytic reaction in first ODH reactor 102. Heated heat-transfer fluid 518 discharges from the jacket 128 through heat exchanger 508 and may return as cooled heat-transfer fluid 519 to the jacket 128.

Heat transfer fluid 504 is supplied to the second-reactor jacket 130 where the heat transfer fluid 504 receives the heat generated by the ODH catalytic reaction in second ODH reactor 104. Heated heat-transfer fluid 524 discharges from the jacket 130 through heat exchanger 510 and may return as cooled heat-transfer fluid 526 to the jacket 130.

Heat transfer fluid 506 is supplied to the third-reactor jacket 132 where the heat transfer fluid 506 receives the heat generated by the ODH catalytic reaction in third ODH reactor 106. Heated heat-transfer fluid 532 discharges from the jacket 132 through heat exchanger 512 and may return as cooled heat-transfer fluid 534 to the jacket 132.

In the illustrated embodiment, the system 700 as depicted employs a single flash vessel 138. Water to be heated to generate steam is supplied to the flash vessel 138 from a water source 140 via pump 142. The water source 140 may include a vessel holding the water to be supplied. The water may be boiler feedwater. A control valve 144 on the conduit conveying the water to the flash vessel 138 may control the flow rate of the water from the source 140 to the flash vessel 138.

Water is provided from the flash vessel 138 to all three depicted heat exchangers 508, 510, 512. The total flow of water discharging from the bottom portion of the flash vessel 138 gives the water 514 stream for the inlet to the first heat exchanger 508, the water 702 stream for the inlet to the second heat exchanger 510, and the water 704 stream for the inlet to the third heat exchanger 512. The water streams flow through the respective heat exchangers 508, 510, 512 and return to the flash vessel 138. The motive force for the three circulation loops of water may be thermosiphon or pump.

The water 514 is heated in the first heat exchanger 518 with heat from the heated heat-transfer fluid 518 discharged from the first-reactor jacket 128. The water 702 is heated in the second heat exchanger 508 with heat from the heated heat-transfer fluid 524 discharged from the second-reactor jacket 130. The water 704 is heated in the third heat exchanger 512 with heat from the heated heat-transfer fluid 532 discharged from the third-reactor jacket 132.

The heat acquired by these water streams that return to the flash vessel promotes (contributes to) the flashing of liquid water in the flash vessel 138 to generate steam 706 that may be a coproduct of the ODH reactor system 700. In embodiments, the steam 706 is high pressure steam at 600 psig or greater. In those embodiments, a portion of the steam 706 may be diverted and let down in pressure via a control valve 708 to give low pressure steam 710 at 150 psig or less. Similarly, a portion of the steam 706 may be diverted and let down in pressure via a control valve 712 to give medium pressure steam 714 in the range of 150 psig to 600 psig or in the range of 250 psig to 400 psig. Both the low pressure steam 710 and the medium pressure steam 714 may be coproducts of the ODH reactor system 700.

Figure 8:
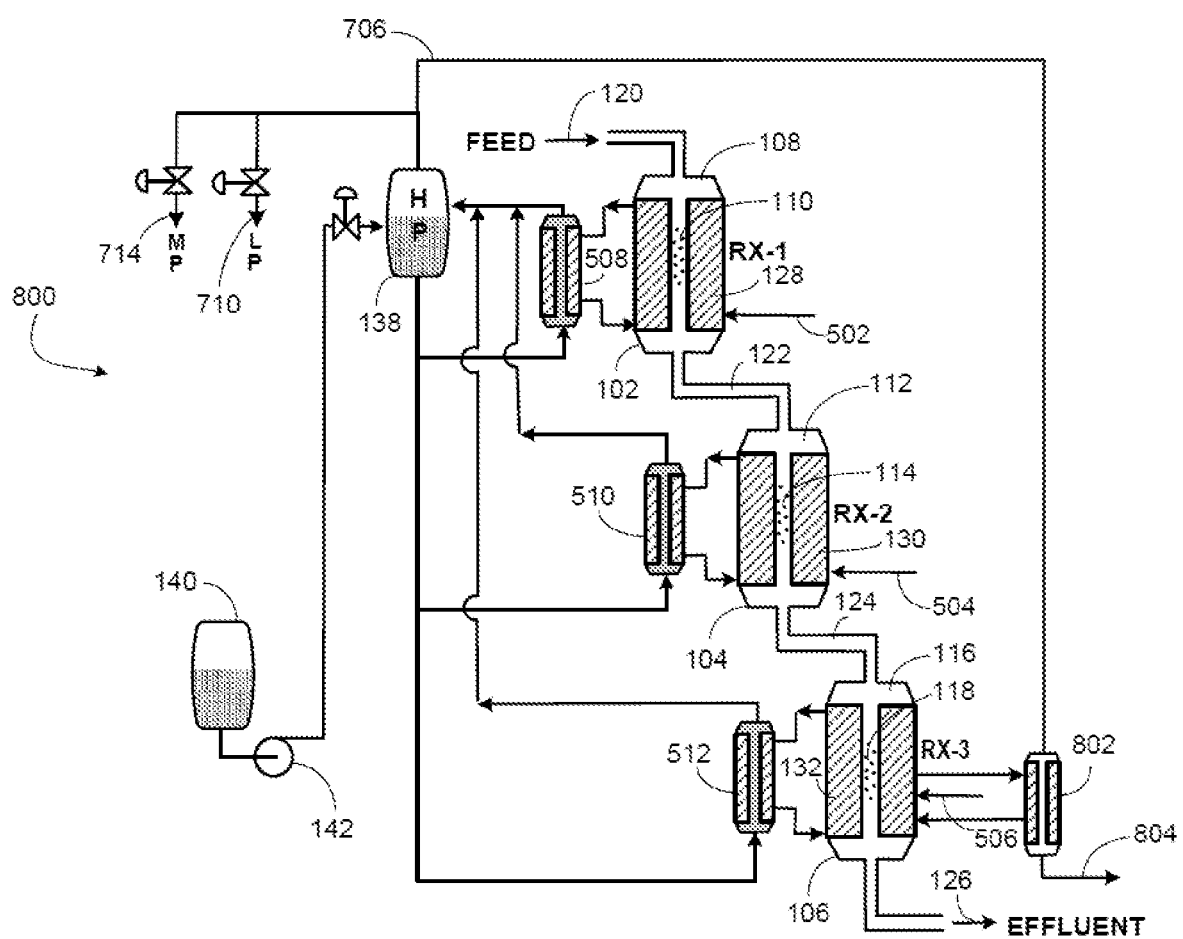

FIG. 8 is an ODH reactor system 800 that is the same as the ODH reactor system of FIG. 7, except that a heat exchanger 802 is incorporated into the system 800 to superheat the high pressure steam 706 so that the coproduct with be superheated steam 804 (e.g., superheated high-pressure steam at 600 psig or greater). In the illustrated embodiment, heat transfer fluid from third-reactor jacket 132 is circulated through the heat exchanger 802 to heat the steam 706. In other embodiments, the third-reactor effluent 126 is instead sent through the heat exchanger 802 as the heat transfer fluid to heat the steam 706. The heat exchanger 802 may be a shell-and-tube heat exchanger or other type of heat exchanger.

Referring to FIGS. 1-8, the feed 120 to the first ODH reactor 102 may be heated (preheated) prior to entry into the first ODH reactor 102. For instance, the feed 120 may be routed through a heat exchanger (e.g., cross exchanger, shell-and-tube heat exchanger, etc.) and heated by the third-reactor effluent 126 routed through the heat exchanger. See, for example, heat exchanger 410 in FIG. 4. Also, at least one of the steam 154, the steam 160, or the steam 166 may be heated in a heat exchanger (e.g., cross exchanger, shell-and-tube heat exchanger, etc.) by the third-reactor effluent 126. The steam 154, steam 160, or steam 166 may be heated to superheat the steam or further superheat the steam. See, for example, the heat exchanger 302 in FIG. 3 that heats the steam 166 to give superheated steam 166. The various embodiments for configuration of the ODH reactor system and steam generation discussed with respect to FIGS. 1-8 are given as examples. Other examples for steam generation by the ODH reactor system will be readily apparent to one of ordinary skill in the art with the benefit of the present disclosure.

Referring to FIGS. 1-8, the catalysts 110, 114, 118 may be the same or different catalyst type. Catalyst types may give different catalytic reaction temperatures in the conversion of the lower alkane to the corresponding alkene. For instance, one catalyst type (labeled, for example, as a low temperature catalyst) may give a catalytic reaction temperature of less than 400° C. Another catalyst type (labeled, for example, as a medium temperature catalyst) may give a catalytic reaction temperature of at least 400° C. (e.g., in the range of 400° C. to 500° C.). Yet another catalyst type (labeled, for example, as a high temperature catalyst) may give a catalytic reaction temperature of at least 500° C.

In some embodiments, the first catalyst 110 is low temperature catalyst (e.g. reaction temperature less than 400° C.), the second catalyst 114 is medium temperature catalyst (e.g., reaction temperature of at least 400° C. or in the range of 400° C. to 500° C.), and the third catalyst 118 is high temperature catalyst (reaction temperature at least 500° C.). In other embodiments, the first catalyst 110 is low temperature catalyst and both the second catalyst 114 and third catalyst 118 are high temperature catalyst. In yet other embodiments, all three catalysts 110, 114, 118 are high temperature catalyst. Other combinations of catalyst types are applicable among the three catalysts 110, 114, 118.

The low temperature catalyst may be conducive for generating low pressure steam (e.g., less than 150 psig). The medium temperature catalyst may be conducive for generating medium pressure steam (e.g., 150 psig to 600 psig). The high temperature catalyst may be conducive for generating high pressure steam (e.g., at least 600 psig). However, each catalyst type may generate heat in its catalytic reaction that can contribute to steam generation of different stream pressures or qualities.

An example of the low temperature catalyst is a catalyst that includes molybdenum, vanadium, tellurium, niobium, and oxygen, wherein the molar ratio of molybdenum to vanadium is from 1:0.12 to 1:0.49, the molar ratio of molybdenum to tellurium is from 1:0.01 to 1:0.30, the molar ratio of molybdenum to niobium is from 1:0.01 to 1:0.30, and oxygen is present at least in an amount to satisfy the valency of any present metal oxides. The molar ratios of molybdenum, vanadium, tellurium, niobium can be determined by inductively coupled plasma mass spectrometry (ICP-MS).

An example of a low temperature catalyst is given in US Published Patent Application No. 2018/0305278 A1, which is incorporated by reference herein in its entirety for all purposes. The catalyst provides for the ODH reaction to at a temperature of less than 400° C. and is available from NOVA Chemicals Corporation having headquarters in Calgary, Canada. This example of a low temperature catalyst is a mixed metal oxide having the formula $Mo_aV_bTe_cNb_dPd_eO_f$, where a, b, c, d, e, and f subscripts are relative atomic amounts of the elements Mo, V, Te, Nb, Pd, O, respectively. When a=1, then b=0.01 to 1.0, c=0.01 to 1.0, d=0.01 to 1.0, 0.00≤e≤0.10, and f is a number to satisfy the valence state of the catalyst.

An example of a medium temperature catalyst is a catalyst labeled as a moderate temperature catalyst in U.S. Pat. No. 9,409,156, which is incorporated by reference herein in its entirety. The catalyst is described as allowing the ODH reaction process to perform in the temperature range of 400° C. to 500° C. An example of a high temperature catalyst is a high temperature catalyst described in International Application Publication No. WO 2013/092179 A1, which is incorporated by reference herein in its entirety. The catalyst is described as allowing the ODH reaction process to run at a temperature in the range of 500° C. to 650° C.

Referring to FIGS. 1-4, for certain cases of the first reactor 102 having a low-temperature ODH catalyst (e.g., providing for an ODH reaction at a temperature of about 400° C. or less), high pressure steam can be generated by the first-reactor 102 system at the first flash vessel 134. However, for other cases of the first reactor 102 having a low-temperature ODH catalyst, the reactor process side temperature may not be adequate to efficiently drive formation of high pressure steam. In other words, the available temperature difference ($\Delta T$) or available log-mean temperature difference (LMTD or $\Delta T_{LM}$) for between the reactor jacket water and the reactor process side may not be adequate to effectively provide for formation of high pressure steam.

Referring to FIGS. 5 and 6, in some examples with the first reactor 102 having a low-temperature ODH catalyst (e.g., providing for an ODH reaction at a temperature of about 400° C. or less), high pressure steam can be generated by the first-reactor 102 system at the first flash vessel 134. However, for other examples of the first reactor 102 having a low-temperature ODH catalyst, the reactor process side temperature may not be adequate to efficiently drive formation of high pressure steam. In other words, the available $\Delta T$ or LMTD for the temperature difference between the water 514, 516 and heat transfer fluid 518, 519 (e.g., molten salt) in the heat exchanger 508 may not be adequate to effectively provide for formation of high pressure steam.

Referring to FIGS. 1-4, implementations employing water (e.g., boiler feedwater) as the heat transfer fluid may be applicable for reactors 102, 104, 106 of small scale. To implement reactors 102, 104, 106 that are large and operating with water at contemplated pressures and temperatures on the reactor jackets 128, 130, 132 (e.g., for the reactor having medium temperature ODH catalyst or high temperature ODH catalyst) may lead to very large or even impractical wall thicknesses of the reactor jackets 128, 130, 132. Therefore, for large reactors, a heat transfer fluid, such as molten salt, may be beneficial for the reactor jackets in certain instances. See, for example, FIGS. 5-8.

Referring to FIGS. 1-8, the first ODH reactor 102, the second ODH reactor 104, and the third ODH reactor 106 may each be a fixed-bed reactor or tubular fixed-bed reactor. For a fixed-bed reactor, reactants may be introduced into the reactor at one end and flow past an immobilized catalyst. Products are formed and an effluent having the products may discharge at the other end of the reactor. The fixed-bed reactor may have one or more tubes (e.g., ceramic tubes) each having a bed of catalyst and for flow of reactants (e.g., lower alkane or ethane) and products (e.g., corresponding alkene or ethylene). The tubes may include, for example, a steel mesh. Moreover, a cooling jacket adjacent the tube(s) may provide for temperature control of the reactor.

In other embodiments, the first ODH reactor 102, the second ODH reactor 104, and the third ODH reactor 106 may each be a fluidized bed reactor. In implementations, a fluidized bed reactor may have a support for the catalyst. The support may be a porous structure or distributor plate and disposed in a bottom portion of the reactor. Reactants may flow upward through the support at a velocity to fluidize the bed of catalyst (e.g., the catalyst rises and begins to swirl around in a fluidized manner). The reactants are converted to products upon contact with the fluidized catalyst. An effluent having products may discharge from an upper portion of the reactor. A cooling jacket may facilitate temperature control of the reactor.

Lastly, the temperature referenced for each reactor (e.g., first temperature in the first reactor, second temperature in the second reactor, and third temperature in the third reactor) may be the temperature at which the respective catalyst drives the oxidative dehydrogenation and may be labeled as the catalyst temperature. The temperature referenced may be the reactor operating temperature driven by the catalytic oxidative dehydrogenation. The temperature referenced may be the weighted average temperature of the reactor or reactor catalyst bed, e.g., over the temperature profile from reactor inlet to reactor outlet. The temperature referenced may be or otherwise incorporate reactor peak temperatures, heat-transfer fluid temperature, temperature of steam generated, and so forth. In certain embodiments, the temperature referenced for each reactor is the maximum temperature within the reactor.

Figure 9:
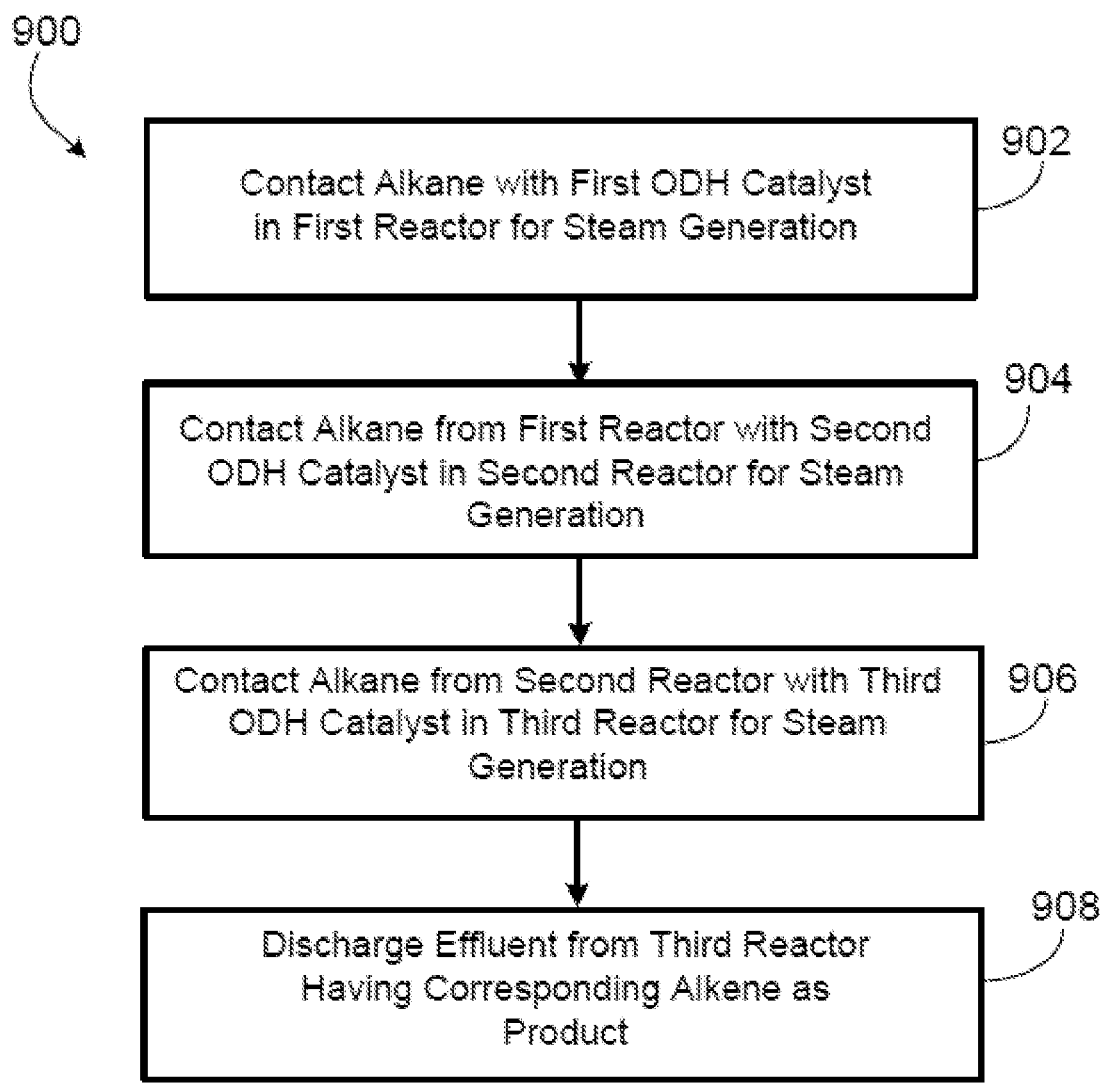
FIG. 9 is a block flow diagram of a method of oxidative dehydrogenation.

FIG. 9 is a method 900 of catalytic oxidative dehydrogenation. The method 900 may be a method of operating an ODH reactor system having at least two ODH reactors disposed in series. Three ODH reactors are discussed with respect to the method 900. However, the present methods may accommodate ODH reactors systems having more than three ODH reactors (e.g., four ODH reactors, five ODH reactors, etc.) in series for the generation of steam. The final ODH reactor in the series may discharge an effluent having a product alkene of the ODH reactor system.

At block 902, the method includes contacting a feed having a lower alkane with a first ODH catalyst in a first reactor at a first temperature (e.g., less than 400° C.) to dehydrogenate the lower alkane into a corresponding alkene and to heat a first heat-transfer fluid flowing through a first-reactor jacket to facilitate generation of steam. The first catalyst may be disposed as a fixed catalyst bed in the first reactor.

At block 904, the method includes contacting a first-reactor effluent from the first reactor with a second ODH catalyst in a second reactor at a second temperature greater than the first temperature to dehydrogenate unreacted lower alkane from the first-reactor effluent into the corresponding alkene and to heat a second heat-transfer fluid flowing through a second-reactor jacket to facilitate generation of steam. The second catalyst may be disposed as a fixed catalyst bed in the second reactor.

At block 906, the method includes contacting a second-reactor effluent from the second reactor with a third ODH catalyst in a third reactor at a third temperature (e.g., at least 500° C.) greater than the first temperature to dehydrogenate unreacted lower alkane from the second effluent into the corresponding alkene and to heat a third heat-transfer fluid flowing through a third-reactor jacket to facilitate generation of steam. The third catalyst may be disposed as a fixed catalyst bed in the third reactor.

For the heat transfer fluid as water, the method may include discharging the first heat-transfer fluid from the first-reactor jacket to a first flash vessel and discharging low pressure steam at 150 psig or less from the first flash vessel.

See, e.g., FIGS. 1-4. The method may include discharging the second heat-transfer fluid from the second-reactor jacket to a second flash vessel and discharging medium pressure steam in the range of 150 psig to 600 psig from the second flash vessel. See, e.g., FIGS. 1-2. The method may include discharging the third heat-transfer fluid from the third-reactor jacket to a third flash vessel and discharging high pressure steam at 600 psig or greater from the third flash vessel. See, e.g., FIGS. 1-2. The method may include discharging water from the first flash vessel as the second heat-transfer fluid to the second-reactor jacket, and discharging water from the second flash vessel as the third heat-transfer fluid to the third-reactor jacket. See, e.g., FIG. 2. In other embodiments, the method may include discharging the second heat-transfer fluid from the second-reactor jacket to the third reactor-jacket as the third heat-transfer fluid, and discharging the third heat-transfer fluid from the third-reactor jacket to a second flash vessel and discharging high pressure steam at 600 psig or greater from the second flash vessel. See, e.g., FIG. 3. In yet other embodiments, the method may include discharging the second heat-transfer fluid from the second-reactor jacket to a second flash vessel, and discharging high pressure steam at 600 psig or greater from the second flash vessel through the third-reactor jacket as the third heat-transfer fluid to superheat the high pressure steam. See, e.g., FIG. 4.

At block 908, the method includes discharging a third-reactor effluent having the corresponding alkene from the third reactor. The corresponding alkene in the third-reactor effluent may be a product of the ODH reactor system having the third reactor, second reactor, and fourth reactor. In some embodiments, the alkane is ethane and the corresponding alkene is ethylene. The first reactor, the second reactor, and the third reactor may each be labeled as an ODH reactor and may each be a tubular fixed-bed reactor. As mentioned, the heat transfer fluid may be water. The heat transfer fluid may be treated water (e.g., demineralized water, boiler feedwater, etc.), synthetic organic compounds, glycol (e.g., ethylene glycol, propylene glycol, etc.), or molten salt.

The method may include discharging the first heat-transfer fluid from the first-reactor jacket to a first heat exchanger and heating, via the first heat exchanger, a first water with the first heat-transfer fluid from the first-reactor jacket. Similarly, the method may include discharging the second heat-transfer fluid from the second-reactor jacket to a second heat exchanger and heating, via the second heat exchanger, a second water with the second heat-transfer fluid from the second-reactor jacket. Likewise, the method may include discharging the third heat-transfer fluid from the third-reactor jacket to a third heat exchanger and heating, via the third heat exchanger, a third water with the third heat-transfer fluid from the first-reactor jacket. See, e.g., FIGS. 5-8. The method may include discharging the first water as heated from the first heat exchanger to a first flash vessel and discharging low pressure steam at 150 psig or less from the first flash vessel. The method may include discharging the second water as heated from the second heat exchanger to a second flash vessel. See, e.g., FIGS. 5-6. The method may include discharging medium pressure steam in the range of 150 psig to 600 psig from the second flash vessel, and discharging the third water as heated from the third heat exchanger to a third flash vessel and discharging high steam at 600 psig or greater from the third flash vessel. See, e.g., FIG. 5. The method may include discharging high pressure steam at 600 psig or greater from the second flash vessel as the third water through the third heat exchanger to superheat the high pressure steam. See, e.g., FIG. 6.

In other embodiments, the method may include discharging the first water as heated by the first heat exchanger to a flash vessel, discharging the second water as heated by the second heat exchanger to the flash vessel, discharging the third water as heated by the third heat exchanger to the flash vessel, and discharging high pressure steam at 600 psig or greater from the flash vessel. See, e.g., FIGS. 7-8. The method may include diverting a portion of the high pressure steam through a control valve to reduce pressure of the portion to medium pressure steam in a range of 150 psig to 600 psig. The method may include diverting a portion of the high pressure steam through a control valve to reduce pressure of the portion to low pressure steam at 150 psig or less. The method may include superheating the high pressure steam in a heat exchanger with heat from the third heat-transfer fluid or from a third-reactor effluent discharged from the third reactor. See, e.g., FIG. 8. The third-reactor effluent may include the corresponding alkene as a product of the ODH reactor system.

An embodiment is an ODH reactor system (e.g., FIGS. 1-8) including a first reactor having a first ODH catalyst to dehydrogenate a lower alkane to a corresponding alkene at a first temperature and facilitate generation of steam. The first reactor has a first-reactor jacket for heat transfer. The ODH reactor system includes a second reactor having a second ODH catalyst to dehydrogenate unreacted lower alkane in a first-reactor effluent from the first reactor to the corresponding alkene at a second temperature greater than the first temperature and facilitate generation of steam. The second reactor has a second-reactor jacket for heat transfer. The ODH reactor system includes a third reactor having a third ODH catalyst to dehydrogenate unreacted lower alkane in a second-reactor effluent from the second reactor to the corresponding alkene at a third temperature greater than the second temperature and facilitate generation of steam. The third reactor has a third-reactor jacket for heat transfer. In implementations, the first ODH catalyst is in a fixed-bed in the first reactor, the second ODH catalyst is in a fixed-bed in the second reactor, the third ODH catalyst is in a fixed-bed in the third reactor, and the third reactor to discharge a third-reactor effluent having the corresponding alkene. In implementations, the first ODH catalyst is different than the second ODH catalyst and the third ODH catalyst, and the second ODH catalyst is different than third ODH catalyst. In some examples, the first temperature is less than 400° C. and the first reactor to facilitate generation of low pressure steam at 150 psig or less, the second temperature is at least 400° C., and the third temperature is at least 500° C. and the third reactor to facilitate generation of high pressure steam of at least 600 psig or very high pressure steam at 1500 psig or greater.

The ODH reactor system may include a first flash vessel (e.g., FIGS. 1-4) to receive jacket water from the first-reactor jacket and discharge low pressure steam at 150 psig or less. If so, the ODH reactor system may include a second flash vessel (e.g., FIGS. 1-2) to receive jacket water from the second-reactor jacket and discharge medium pressure steam in a range of 150 psig to 600 psig or discharge high pressure steam at 600 psig or greater. A third flash vessel (e.g., FIGS. 1-2) may receive jacket water from the third-reactor jacket and discharge high pressure steam at 600 psig or greater or discharge very high pressure steam at 1500 psig or greater. In other examples, a second flash vessel (e.g., FIG. 3) receives jacket water from the third-reactor jacket and discharges high pressure steam at 600 psig or greater. In yet other examples, a second flash vessel (e.g., FIG. 4) receives jacket water from the second-reactor jacket and discharges high pressure steam at 600 psig or greater (or very high pressure steam at 1500 psig or greater) and discharges the steam through the third-reactor jacket to superheat the steam.

The ODH reactor system (e.g., FIGS. 5-8) may include: a first heat exchanger to heat a first water with heat transfer fluid from the first-reactor jacket; a second heat exchanger to heat a second water with heat transfer fluid from the second-reactor jacket; and a third heat exchanger to heat a third water with heat transfer fluid from the third-reactor jacket. In certain implementations (e.g., FIG. 5), the ODH reactor system includes: a first flash vessel to receive the first water as heated from the first heat exchanger and discharge low pressure steam at 150 psig or less; a second flash vessel to receive the second water as heated from the second heat exchanger and discharge medium pressure steam in the range 150 psig to 600 psig or high pressure steam at 600 psig or greater; and a third flash vessel to receive the third water as heated from the third heat exchanger and discharge high pressure steam at 600 psig or greater or very high pressure steam at 1500 psig or greater. In some implementations (e.g., FIG. 6), the ODH reactor system includes: a first flash vessel to receive the first water as heated from the first heat exchanger and discharge low pressure steam at 150 psig or less; and a second flash vessel to receive the second water as heated from the second heat exchanger and discharge high pressure steam at 600 psig or greater as the third water through the third heat exchanger to superheat the high pressure steam. In other implementations (e.g., FIGS. 7-8), the ODH reactor system includes a flash vessel to receive the first water as heated by the first heat exchanger, the second water as heated by the second heat exchanger, and the third water as heated by the third heat exchanger, and discharge high pressure steam at 600 psig or greater. If so, the system (e.g., FIGS. 7-8) may include a control valve to reduce pressure of a portion of the high pressure steam to medium pressure steam in a range of 150 psig to 600 psig, and also include a control valve to reduce pressure of a portion of the high pressure steam to low pressure steam at 150 psig or less. The ODH reactor system (e.g., FIG. 8) may have a heat exchanger to superheat the high pressure steam with heat from the heat transfer fluid from the third-reactor jacket or with heat from a third-reactor effluent discharged from the third reactor. The third-reactor effluent may have the corresponding alkene as a product of the ODH reactor system.

Another embodiment is a system for oxidative dehydrogenation, including a first reactor having first ODH catalyst to dehydrogenate an alkane at a first temperature. The alkane may have a number of carbons in a range of two carbons to six carbons. The first reactor has a first-reactor jacket to heat a first heat-transfer fluid flowing through the first-reactor jacket to facilitate generation of the steam. The system includes a second reactor having a second ODH catalyst to dehydrogenate unreacted alkane from the first reactor at a second temperature greater than the first temperature. The second reactor has a second-reactor jacket to heat a second heat-transfer fluid flowing through the second-reactor jacket to facilitate generation of steam. A third reactor has a third ODH catalyst to dehydrogenate unreacted alkane from the second reactor at a third temperature greater than the first temperature. The third reactor has a third-reactor jacket to heat a third heat-transfer fluid flowing through the third-reactor jacket to facilitate generation of steam. The third ODH catalyst and the second ODH catalyst are different than the first ODH catalyst. The third ODH catalyst may be different than the second ODH catalyst. Moreover, the first reactor, the second reactor, and the third reactor may each be a tubular fixed-bed reactor. Lastly, the system for oxidative dehydrogenation may include an ODH reactor system having the first reactor, the second reactor, and the third reactor, and wherein the ODH reactor system to generate high pressure steam at 600 psig or greater, or very high pressure steam at 1500 psig or greater.

Yet another embodiment is a method of oxidative dehydrogenation. The method (e.g., FIGS. 1-9) includes: contacting a feed having a lower alkane (e.g., ethane) with a first ODH catalyst in a first reactor at a first temperature (e.g., less than 400° C.) to dehydrogenate the lower alkane into a corresponding alkene (e.g., ethylene) and to heat a first heat-transfer fluid flowing through a first-reactor jacket to facilitate generation of steam; contacting a first-reactor effluent from the first reactor with a second ODH catalyst in a second reactor at a second temperature (e.g., at least 400° C.) greater than the first temperature to dehydrogenate unreacted lower alkane from the first-reactor effluent into the corresponding alkene and to heat a second heat-transfer fluid flowing through a second-reactor jacket to facilitate generation of steam; and contacting a second-reactor effluent from the second reactor with a third ODH catalyst in a third reactor at a third temperature (e.g., at least 500° C.) greater than the first temperature to dehydrogenate unreacted lower alkane from the second effluent into the corresponding alkene and to heat a third heat-transfer fluid flowing through a third-reactor jacket to facilitate generation of steam. In examples, the first temperature is less than 400° C., the second temperature is at least 400° C. (or in the range of 400° C. to 500° C.), and the third temperature is at least 400° C. The method may include discharging a third-reactor effluent from the third reactor, wherein the third-reactor effluent includes the corresponding alkene. In implementations, the first reactor, the second reactor, and the third reactor are each a tubular fixed-bed reactor.

The method (e.g., FIGS. 1-4 and 9) may include discharging the first heat-transfer fluid from the first-reactor jacket to a first flash vessel (wherein the first heat-transfer fluid is water or primarily water) and discharging low pressure steam at 150 psig or less from the first flash vessel. If so, the method (e.g., FIGS. 1-2 and 9) may include: discharging the second heat-transfer fluid (water or primarily water) from the second-reactor jacket to a second flash vessel; discharging medium pressure steam in the range of 150 psig to 600 psig from the second flash vessel; discharging the third heat-transfer fluid (water or primarily water) from the third-reactor jacket to a third flash vessel; and discharging high pressure steam at 600 psig or greater (or very high pressure steam at 1500 psig or greater) from the third flash vessel. In certain implementations (e.g., FIGS. 2 and 9), the method includes discharging water from the first flash vessel as the second heat-transfer fluid to the second-reactor jacket; and discharging water from the second flash vessel as the third heat-transfer fluid to the third-reactor jacket. In other implementations (e.g., FIGS. 3 and 9), the method includes: discharging the second heat-transfer fluid from the second-reactor jacket (water or primarily water) to the third reactor-jacket as the third heat-transfer fluid; discharging the third heat-transfer fluid from the third-reactor jacket to a second flash vessel; and discharging high pressure steam at 600 psig or greater (or very high pressure steam at 1500 psig or greater) from the second flash vessel. In yet other implementations (e.g., FIGS. 4 and 9), the method include: discharging the second heat-transfer fluid from the second-reactor jacket to a second flash vessel; and discharging high pressure steam at 600 psig or greater (or very high pressure steam at 1500 psig or greater) from the second flash vessel through the third-reactor jacket as the third heat-transfer fluid to superheat the high pressure steam (or very high pressure steam).

In some implementations (e.g., FIGS. 5-9), the method includes: discharging the first heat-transfer fluid from the first-reactor jacket to a first heat exchanger and heating, via the first heat exchanger, a first water with the first heat-transfer fluid from the first-reactor jacket; discharging the second heat-transfer fluid from the second-reactor jacket to a second heat exchanger and heating, via the second heat exchanger, a second water with the second heat-transfer fluid from the second-reactor jacket; and discharging the third heat-transfer fluid from the third-reactor jacket to a third heat exchanger and heating, via the third heat exchanger, a third water with the third heat-transfer fluid from the first-reactor jacket. The method (e.g., FIGS. 5-6 and 9) may include discharging the first water as heated from the first heat exchanger to a first flash vessel, discharging low pressure steam at 150 psig or less from the first flash vessel, and discharging the second water as heated from the second heat exchanger to a second flash vessel. If so, the method (e.g., FIGS. 5 and 9) may include discharging medium pressure steam in the range of 150 psig to 600 psig (or high pressure steam at 600 psig or greater) from the second flash vessel, discharging the third water as heated from the third heat exchanger to a third flash vessel, and discharging high pressure steam at 600 psig or greater (or very high pressure steam at 1500 psig or greater) from the third flash vessel. The method (e.g., FIGS. 5 and 9) may include discharging high pressure steam at 600 psig or greater (or very high pressure steam at 1500 psig or greater) from the second flash vessel as the third water through the third heat exchanger to superheat the high pressure steam.

In implementations (e.g., FIGS. 7-9), the method may include: discharging the first water as heated by the first heat exchanger to a flash vessel; discharging the second water as heated by the second heat exchanger to the flash vessel; discharging the third water as heated by the third heat exchanger to the flash vessel; and discharging high pressure steam at 600 psig or greater (or very high pressure steam at 1500 psig or greater) from the flash vessel. The method may include diverting a portion of the high pressure steam (or very high pressure steam) through a control valve to reduce pressure of the portion to medium pressure steam in a range of 150 psig to 600 psig. The method may include diverting a portion of the high pressure steam (or very high pressure steam) through a control valve to reduce pressure of the portion to medium pressure steam in a range of 150 psig to 600 psig to low pressure steam at 150 psig or less. The method (e.g., FIGS. 8-9) may include superheating the high pressure steam in a heat exchanger with heat from the third heat-transfer fluid or from a third-reactor effluent discharged from the third reactor. The third-reactor effluent may include the corresponding alkene as a product of the ODH reactor system.

A number of implementations have been described. Nevertheless, it will be understood that various modifications may be made without departing from the spirit and scope of the disclosure.

INDUSTRIAL APPLICABILITY

Oxidative dehydrogenation of alkanes into their corresponding alkenes.

The invention claimed is:
1. A system, comprising:
a first reactor comprising a first oxidative dehydrogenation (ODH) catalyst configured to dehydrogenate a lower alkane to a corresponding alkene at a first temperature and to facilitate generation of steam, wherein the first reactor comprises a first-reactor jacket configured to transfer heat;
a second reactor comprising a second ODH catalyst configured to dehydrogenate unreacted lower alkane in a first-reactor effluent from the first reactor to the corresponding alkene at a second temperature greater than the first temperature and to facilitate generation of steam, wherein the second reactor comprises a second-reactor jacket configured to transfer heat; and
a third reactor comprising a third ODH catalyst configured to dehydrogenate unreacted lower alkane in a second-reactor effluent from the second reactor to the corresponding alkene at a third temperature greater than the second temperature and to facilitate generation of steam, wherein the third reactor comprises a third-reactor jacket configured to transfer heat,
wherein the first ODH catalyst is in a fixed-bed in the first reactor, the second ODH catalyst is in a fixed-bed in the second reactor, the third ODH catalyst is in a fixed-bed in the third reactor, and the third reactor is configured to discharge a third-reactor effluent comprising the corresponding alkene.

2. The system of claim 1, wherein the first ODH catalyst is different from the second ODH catalyst and the third ODH catalyst, and the second ODH catalyst is different from third ODH catalyst.

3. The system of claim 1, wherein the first temperature is less than 400° C., the first reactor is configured to facilitate generation of steam at 150 pounds per square inch (psig) or less, the second temperature is at least 400° C., the third temperature is at least 500° C., and the third reactor is configured to facilitate generation of steam of at least 600 psig.

4. The system of claim 1, further comprising a first flash vessel configured to receive jacket water from the first-reactor jacket and to discharge steam at 150 pounds per square inch (psig) or less.

5. The system of claim 4, further comprising:
a second flash vessel configured to receive jacket water from the second-reactor jacket and to discharge steam in a range of 150 psig to 600 psig; and
a third flash vessel configured to receive jacket water from the third-reactor jacket and to discharge steam at 600 psig or greater.

6. The system of claim 4, further comprising a second flash vessel configured to receive jacket water from the third-reactor jacket and to discharge steam at 600 psig or greater.

7. The system of claim 4, further comprising a second flash vessel to receive jacket water from the second-reactor jacket and to discharge steam at 600 psig or greater.

8. The system of claim 7, wherein the second flash vessel is configured to discharge the steam through the third-reactor jacket to superheat the steam.

9. The system of claim 1, further comprising:
a first heat exchanger configured to heat a first water with heat transfer fluid from the first-reactor jacket;
a second heat exchanger configured to heat a second water with heat transfer fluid from the second-reactor jacket; and
a third heat exchanger configured to heat a third water with heat transfer fluid from the third-reactor jacket.

10. The system of claim 9, further comprising:
a first flash vessel configured to receive the heated first water from the first heat exchanger and to discharge steam at 150 pounds per square inch (psig) or less;

a second flash vessel configured to receive the heated second water from the second heat exchanger and to discharge steam at 150 psig or greater; and a third flash vessel configured to receive the heated third water from the third heat exchanger and to discharge steam at 600 psig or greater.

11. The system of claim 9, further comprising:

a first flash vessel to receive the heated first water from the first heat exchanger and to discharge steam at 150 psig or less; and a second flash vessel to receive the heated second water from the second heat exchanger and to discharge steam at 600 psig or greater as the third water through the third heat exchanger to superheat the steam at 600 psig or greater.

12. The system of claim 9, further comprising a flash vessel configured to receive the first water as heated by the first heat exchanger, the second water as heated by the second heat exchanger, and the third water as heated by the third heat exchanger, wherein the flash vessel is configured to discharge steam at 600 psig or greater.

13. The system of claim 12, further comprising a control valve configured to reduce a pressure of a portion of the steam at a pressure of 600 psig or greater to steam having a pressure in a range of 150 psig to 600 psig.

14. The system of claim 12, further comprising a control valve configured to reduce pressure of a portion of the steam at a pressure of 600 psig or greater to steam having a pressure of 150 psig or less.

15. The system of claim 12, further comprising a heat exchanger configured to superheat the steam at 600 psig or greater with heat from the heat transfer fluid from the third-reactor jacket or with heat from a third-reactor effluent discharged from the third reactor, the third-reactor effluent comprising the corresponding alkene as a product of the system.

16. A system, comprising:

a first reactor comprising a first oxidative dehydrogenation (ODH) catalyst configured to dehydrogenate an alkane at a first temperature, wherein the first reactor comprises a first-reactor jacket configured to heat a first heat-transfer fluid flowing through the first-reactor jacket to facilitate generation of steam;

a second reactor comprising a second ODH catalyst configured to dehydrogenate unreacted alkane from the first reactor at a second temperature greater than the first temperature, wherein the second reactor comprises a second-reactor jacket configured to heat a second heat-transfer fluid flowing through the second-reactor jacket to facilitate generation of steam; and a third reactor comprising a third ODH catalyst configured to dehydrogenate unreacted alkane from the second reactor at a third temperature greater than the first temperature, wherein the third reactor comprises a third-reactor jacket to heat a third heat-transfer fluid flowing through the third-reactor jacket to facilitate generation of steam, and the third ODH catalyst and the second ODH catalyst are different from the first ODH catalyst, wherein the first ODH catalyst is in a fixed-bed in the first reactor, the second ODH catalyst is in a fixed-bed in the second reactor, the third ODH catalyst is in a fixed-bed in the third reactor, and the third reactor is configured to discharge a third-reactor effluent comprising the corresponding dehydrogenated alkane.

17. The system of claim 16, wherein the third ODH catalyst is different from the second ODH catalyst, and the third temperature is greater than the first temperature.

18. The system of claim 16, wherein the system for oxidative dehydrogenation comprises an ODH reactor system comprising the first reactor, the second reactor, and the third reactor, and wherein the ODH reactor system is configured to generate steam at 600 pounds per square inch gauge (psig) or greater.

19. The system of claim 16, wherein the alkane comprises a number of carbons in a range of two carbons to six carbons, wherein the first reactor, the second reactor, and the third reactor each comprise a tubular fixed-bed reactor.

\* \* \* \* \*